United States Patent [19]

Fischbach et al.

[11] Patent Number: 5,665,862
[45] Date of Patent: Sep. 9, 1997

[54] NEUROTROPHIC FACTOR

[75] Inventors: Gerald D. Fischbach, Cambridge; Douglas L. Falls, Natick; Kenneth M. Rosen, West Roxbury; Gabriel Corfas, Brookline, all of Mass.

[73] Assignee: President and Fellows of Harvard College, Cambridge, Mass.

[21] Appl. No.: 168,091

[22] Filed: Dec. 15, 1993

Related U.S. Application Data

[63] Continuation-in-part of Ser. No. 953,742, Sep. 29, 1992, abandoned.

[51] Int. Cl.$^6$ .................. C07K 14/435; C07K 14/475
[52] U.S. Cl. ............... 530/350; 530/324; 530/395; 530/399
[58] Field of Search ................... 530/350, 399, 530/395, 387.11, 324; 435/6

[56] References Cited

U.S. PATENT DOCUMENTS 5,237,056  8/1993  Fischbach ..................... 536/23.5

FOREIGN PATENT DOCUMENTS

WO 91/15230  10/1991  WIPO.

OTHER PUBLICATIONS

Buc–Caron et al., "Induction of Acetylcholine Receptor Synthesis and Aggregation: Partial Purification of Low–Molecular–Weight Activity" *Developmental Biology*, vol. 95, pp. 378–386, 1983.

Burgen et al., "Development of Ideas Abuot Cholinergic Transmission" *Life Sciences*, vol. 50, pp. PL–01–PL–99, 1992.

Carr et al., "A Novel 87,000–M$_4$Protein Associated with Acetylcholine Receptors in Torpedo Electric Organ and Vertebrate Skeletal Muscle" *The Journal of Cell Biology*, vol. 109, pp. 1753–1764, Oct. 1989.

Cohen et al., "Expressionj of the neu Proto–Oncogene by Schwann Cells During Peripheral Nerve Development and Walledan Degeneration" *Journal of Neuroscience Research*, vol. 31, pp. 622–634, 1992.

Connolly et al., "Extracts of Electric Lobe and Electric Organ from *Torpedo Californica* increase the total number as well as the number of Aggregates of Chick Myotube Acetylcholine Receptors" *The Journal of Neuroscience*, vol. 2, No. 9, pp. 1207–1213, Sep. 1982.

Corfas et al., "The Number of Na$^+$Channels in Cultured Chick Muscle Is Increased by ARIA, an Acetylcholine Receptor–inducing Activity" *The Journal of Neuroscience*, vol. 13, No. 5, pp. 2118–2125.

Corfas et al., "ARIA, a protein that stimulates acetylcholine receptor synthesis, also induces tyrosine phosphorylation of a 185–kDa muscle transmembrane protein" *Proceedings of the National Academy of Sciences*, vol. 90, pp. 1624–1628, Feb. 1993.

Di Fiore et al., "EGF Receptor and erbB–2 Tyrosine Kinase Domains Confer Cell Specificity for Mitogenic Signaling" *Science*, vol. 248, pp. 79–83, Apr. 6, 1990.

Dubinsky et al., "Formation of Acetylcholine Receptor Clusters in Chick Myotubes: Migration or New Insertion?"*The Journal of Cell Biology*, vol. 109, pp. 1733–1743, Oct. 1989.

Dubinsky et al., "Variation among Acetylcholine Receptor Clusters Induced by Ciliari Ganglion Neurons in Vitro" *Developmental Biology*, vol. 130, pp. 209–219, 1988.

Engisch et al., "The Development of ACH–and GABA–activated Currents in Embryonic Chick Ciliary Ganglion Neurons in the Absence on Innervation in vivo" *The Journal of Neuroscience*, vol. 12, No. 3, pp. 115–125, March 1992.

Engisch et al., "The Development of ACH–and GABA–activated Currents in Normal and Target–Deprived Embryonic Chick Ciliary Ganglia" *Developmental Biology*, vol. 139, pp. 417–426, 1990.

Falls et al., "ARIA, a Protein That Stimulates Acetylcholine Receptor Synthesis Acetylcholine Receptor Synthesis, Is a Member of the Neu Ligand Family" *Cell*, vol. 72, pp. 801–815, Mar. 12, 1993.

Falls et al., "M$_r$42,000 ARIA: A Protein That May Regulate the Accumulation of Acetylcholine Receptor at Developing Chick Neuromuscular Junctions" *Cold Spring Harbor Symposia on Quantitative Biology*, vol. LV, pp. 397–405, 1990.

Harris et al., "A prion–like protein from chicken brain copurifies with an acetylcholine receptor–inducing activity" *Proceedings of the National Academy of Sciences*, vol. 88, pp. 7664–7668, Sep. 1991.

Harris et al., "Differential activation of mytotube nuclei following exposure to an acetylcholine receptor–inducing factor" *Nature Letters*, vol. 337, pp. 173–176, Jan. 12, 1989.

Harris et al., "Acetylcholine receptor–inducing factor from chicken brain increases the level of mRNA encoding the receptor α subunit" *Proceedings of the National Academy of Sciences*, vol. 85, pp. 1983–1987, Mar. 1988.

Holmes et al., "Identification of Heregulin, a Specific Activator of p185$^{erbB2}$" *Science*, vol. 256, pp. 1205–1210, May 22, 1992.

Kimura et al., "Structure, expression and function of a shwannoma–derived growth factor" *Nature Letters*, vol. 348, pp. 257–260, Nov. 15, 1990.

(List continued on next page.)

*Primary Examiner*—Marianne P. Allen

[57] ABSTRACT

The invention pertains to isolated neurotrophic factors, designated as ARIA, which are able to induce the formation of ion channels in a surface membrane of a cell. The amino acid sequence of the neurotrophic factors includes an EGF-like domain, and a second amino acid sequence encoded by at least a portion of an exon of the neurotrophic factor gene normally expressed in a neuronal cell, especially a nerve cell. The neurotrophic factor is distinct from, and essentially unrelated to, the chicken prion-like protein previously identified.

12 Claims, 6 Drawing Sheets

OTHER PUBLICATIONS

Lemke et al., "Developmental Neurobiology. Recitative and ARIA" *Nature*, vol. 362, No. 6418, pp. 291–292, Mar. 25, 1993.

Lupu et al., "Direct Interaction of a Ligand for the erbB2 Oncogene Product with the EGF Receptor and p185$^{erbB2}$" *Science*, vol. 249, pp. 1552–1555, Sep. 28, 1990.

Marchionni et al., "Glial growth factors are alternatively spliced erbB2 ligands expressed in the nervous system" *Nature*, vol. 362, No. 6418, 312–318, Mar. 25, 1993.

Martinou et al., "Cholinergic Differentiation Factor (CDF/LIF) Promotes Survival of Isolated Rat Embryonic Motoneurons In Vitro" *Neuron*, vol. 8 Apr. 1992, pp.737–744.

Martinou et al., "Acetychloine receptor–inducing activity stimulates expression of the E–subunit gene of the muscle acetylcholine receptor" *Proceedings of the National Academy of Sciences*, vol. 88, pp. 7669–7673, Sep. 1992.

Peles et al., "Isolation of the Neu/HER–2 Stimulatory Ligand: A 44 kd Glycoprotein That Induces Differentiation of Mammary Tumor Cells" *Cell*, vol. 69, pp. 205–216, 3 Apr. 1992.

Prigent and Lemoine, "The Type 1 (EGFR–Related Family of Growth Factor Receptors and Their Ligands" *Progress in Growth Factor Research*, vol. 4., pp. 1–24, 1992.

Role and Fischbach, "Changes in the Number of Chick Ciliary Ganglion Neuron Processes with Time in Cell Culture" *Journal of Cell Biology*, vol. 104, pp. 363–370, Feb. 1987.

Role et al., "The Distribution of Acetycholine Receptor Clusters and Sites of Transmitter Release along Chick Ciliary Ganglion Neurite–Myotube Contacts in Culture" *Journal of Cell Biology*, vol. 104, pp. 371–379, Feb. 1987.

Role et al., "On the Mechanism of Acetylcholine Receptor Accumulation at Newly Formed Synapses on Chick Myotubes" *Journal of Neuroscience*, vol 5, pp. 2197–2204, Aug. 1985.

Siegel and Fischbach, "Muscarinic Receptors and Responses in Intact Embryonic Chick Atrial and Ventricular Heart Cells" *Developmental Biology*, vol. 101, pp. 346–356, 1984.

Tsui et al, "Variation in the Ratio of Acetylcholine Receptors and the Mr43,000 Receptor–Associated Protein in Embryonic Chick Myotubes and Myoblasts" *Developmental Biology*, vol. 140, pp.437–446, 1990.

Usdin and Fischbach, "Purification and Characterization of a Polypeptide from Chick Brain that Promotes the Accumulation of Acetylcholine Receptors in Chick Myotubes" *Journal of Cell Biology*, vol. 103, Aug. 1986.

Wen, Duanzhi et al., "Neu Differentiation Factor: A Transmembrane Glycoprotein Containing an EGF Domain and an Immunoglobulin Homology Unit" *Cell*, vol. 69, pp. 559–572, 1 May 1992.

Yarden and Peles, "Biochemical Analysis of the Ligand for the neu Oncogenic Receptor" *Biochemistry*, vol. 30, pp. 3543–3550, 1991.

FIGURE 1A

```
GAATTCCGGC GTCCTGCGGG GG ATG TGG GCC ACC TCT GAA GGT CCA CTT CAG       52
                          Met Trp Ala Thr Ser Glu Gly Pro Leu Gln
                           1                5                  10

TAC AGC CTG GCA CCA ACA CAG ACG GAC GTC AAC AGC AGT TAC AGC ACA       100
Tyr Ser Leu Ala Pro Thr Gln Thr Asp Val Asn Ser Ser Tyr Ser Thr
            15                  20                  25

GTG CCT CCC AAA TTG AAG GAA ATG GAA AAC CAA GAG GTT GCT GTG GGT       148
Val Pro Pro Lys Leu Lys Glu Met Glu Asn Gln Glu Val Ala Val Gly
              30                  35                  40

CAG AAG CTA GTG CTA AGG TGT GAA ACC ACT TCA GAG TAC CCT GCG CTC       196
Gln Lys Leu Val Leu Arg Cys Glu Thr Thr Ser Glu Tyr Pro Ala Leu
         45                  50                  55

AGA TTC AAA TGG TTA AAG AAC GGG AAG GAA ATA ACG AAA AAA AAC AGA       244
Arg Phe Lys Trp Leu Lys Asn Gly Lys Glu Ile Thr Lys Lys Asn Arg
         60                  65                  70

CCC GAA AAT GTC AAG ATC CCC AAA AAG CAA AAG AAA TAC TCT GAG CTT       292
Pro Glu Asn Val Lys Ile Pro Lys Lys Gln Lys Lys Tyr Ser Glu Leu
 75                  80                  85                  90

CAT ATT TAT AGG GCC ACG TTG GCT GAC GCT GGG GAA TAC GCA TGC AGA       340
His Ile Tyr Arg Ala Thr Leu Ala Asp Ala Gly Glu Tyr Ala Cys Arg
                 95                 100                 105

GTG AGC AGC AAA CTA GGG AAC GAC AGT ACT AAA GCA AGT GTT ATC ATC       388
Val Ser Ser Lys Leu Gly Asn Asp Ser Thr Lys Ala Ser Val Ile Ile
             110                 115                 120

ACA GAC ACC AAT GCC ACT TCT ACA TCT ACA ACT GGG ACA AGT CAT CTC       436
Thr Asp Thr Asn Ala Thr Ser Thr Ser Thr Thr Gly Thr Ser His Leu
         125                 130                 135

ACA AAA TGT GAC ATA AAG CAG AAA GCC TTC TGT GTA AAT GGG GGA GAG       484
Thr Lys Cys Asp Ile Lys Gln Lys Ala Phe Cys Val Asn Gly Gly Glu
     140                 145                 150

TGC TAC ATG GTT AAA GAC CTC CCA AAC CCT CCA CGA TAC CTA TGC AGG       532
Cys Tyr Met Val Lys Asp Leu Pro Asn Pro Pro Arg Tyr Leu Cys Arg
155                 160                 165                 170

TGC CCA AAT GAA TTT ACT GGT GAT CGC TGC CAA AAC TAC GTA ATG GCC       580
Cys Pro Asn Glu Phe Thr Gly Asp Arg Cys Gln Asn Tyr Val Met Ala
                     175                 180                 185

AGC TTC TAC AAG CAT CTT GGG ATT GAA TTT ATG GAA GCT GAG GAA CTG       628
Ser Phe Tyr Lys His Leu Gly Ile Glu Phe Met Glu Ala Glu Glu Leu
                 190                 195                 200
```

FIGURE 1B

```
         TAC CAG AAA CGG⎡⑤GTG CTG ACC ATA ACT GGC ATT TGC ATT GCT CTT CTA        676
         Tyr Gln Lys Arg Val Leu Thr Ile Thr Gly Ile Cys Ile Ala Leu Leu
                 205       210                   215
                                              ⑤
         GTA GTT GGC ATC ATG TGT GTG GTG GCC TAC TGC⎤AAA ACC AAG AAG CAG         724
         Val Val Gly Ile Met Cys Val Val Ala Tyr Cys Lys Thr Lys Lys Gln
             220             225               ⎦230

AGG AAA AAG TTG CAT GAC CGC CTT CGG CAG AGC CTT CGC TCA GAG AGG         772
         Arg Lys Lys Leu His Asp Arg Leu Arg Gln Ser Leu Arg Ser Glu Arg
         235             240                 245                 250

AAC AAC GTT ATG AAC ATG GCA AAT GGG CCA CAC CAC CCC AAC CCA CCA         820
         Asn Asn Val Met Asn Met Ala Asn Gly Pro His His Pro Asn Pro Pro
                         255                 260                 265

CCA GAC AAT GTC CAG CTG GTG AAT CAG TAC GTT TCA AAA AAC ATA ATC         868
         Pro Asp Asn Val Gln Leu Val Asn Gln Tyr Val Ser Lys Asn Ile Ile
                     270                 275                 280

TCC AGT GAA CGT GTC GTT GAG CGA GAA ACC GAG ACC TCG TTT TCC ACA         916
         Ser Ser Glu Arg Val Val Glu Arg Glu Thr Glu Thr Ser Phe Ser Thr
                 285                 290                 295

AGC CAC TAC ACC TCA ACA ACT CAT CAC TCC ATG ACA GTC ACC CAG ACG         964
         Ser His Tyr Thr Ser Thr Thr His His Ser Met Thr Val Thr Gln Thr
             300                 305                 310

CCT AGC CAC AGC TGG AGT AAT GGC CAT ACC GAA AGC ATT CTC TCC GAA        1012
         Pro Ser His Ser Trp Ser Asn Gly His Thr Glu Ser Ile Leu Ser Glu
         315                 320                 325                 330

AGC CAC TCC GTG CTC GTC AGC TCC TCA GTG GAG AAT AGC AGG CAC ACC        1060
         Ser His Ser Val Leu Val Ser Ser Ser Val Glu Asn Ser Arg His Thr
                         335                 340                 345

AGC CCA ACA GGG CCA CGA GGC CGC CTC AAT GGN ATT GGT GGG CCA AGG        1108
         Ser Pro Thr Gly Pro Arg Gly Arg Leu Asn Gly Ile Gly Gly Pro Arg
                     350                 355                 360

GAA GGC AAC AGC TTC CTC CGG CAT GCA AGA GAG ACC CCT GAC TCC TAC        1156
         Glu Gly Asn Ser Phe Leu Arg His Ala Arg Glu Thr Pro Asp Ser Tyr
                 365                 370                 375

CGA GAC TCT CCT CAC AGT GAA AGG TAT GTC TCA GCT ATG ACC ACA CCA        1204
         Arg Asp Ser Pro His Ser Glu Arg Tyr Val Ser Ala Met Thr Thr Pro
             380                 385                 390

GCT CGC ATG TCA CCC GTT GAT TTC CAC ACT CCA ACT TCT CCC AAG TCC        1252
         Ala Arg Met Ser Pro Val Asp Phe His Thr Pro Thr Ser Pro Lys Ser
         395                 400                 405                 410
```

FIGURE 1C

```
CCT CCA TCT GAA ATG TCA CCA CCA GTT TCC AGC TTG ACC ATC TCC ATC      1300
Pro Pro Ser Glu Met Ser Pro Pro Val Ser Ser Leu Thr Ile Ser Ile
            415             420                 425

CCT TCG GTG GCG GTG AGT CCC TTT ATG GAC GAG GAG AGA CCG CTG CTG      1348
Pro Ser Val Ala Val Ser Pro Phe Met Asp Glu Glu Arg Pro Leu Leu
            430             435                 440

TTG GTG ACC CCA CCA CGG CTG CGT GAG AAG TAC GAC AAC CAC CTT CAG      1396
Leu Val Thr Pro Pro Arg Leu Arg Glu Lys Tyr Asp Asn His Leu Gln
            445             450                 455

CAA TTC AAC TCC TTC CAC AAC AAT CCC ACC CAT GAG AGC AAC AGT CTG      1444
Gln Phe Asn Ser Phe His Asn Asn Pro Thr His Glu Ser Asn Ser Leu
            460             465                 470

CCA CCC AGT CCT CTG AGG ATA GTG GAG GAT GAA GAG TAT GAG ACC ACG      1492
Pro Pro Ser Pro Leu Arg Ile Val Glu Asp Glu Glu Tyr Glu Thr Thr
475             480                 485                 490

CAG GAG TAC GAA CCA GCA CAG GAG CCT CCA AAG AAA CTC ACC AAC AGC      1540
Gln Glu Tyr Glu Pro Ala Gln Glu Pro Pro Lys Lys Leu Thr Asn Ser
                495             500                 505

CGG AGG GTG AAA AGA ACA AAG CCC AAT GGC CAT ATT TCC AGC AGG GTA      1588
Arg Arg Val Lys Arg Thr Lys Pro Asn Gly His Ile Ser Ser Arg Val
            510             515                 520

GAA GTG GAC TCC GAC ACA AGC TCT CAG AGC ACT AGC TCT GAG AGC GAA      1636
Glu Val Asp Ser Asp Thr Ser Ser Gln Ser Thr Ser Ser Glu Ser Glu
            525             530                 535

ACA GAA GAT GAA AGA ATA GGT GAG GAT ACA CCA TTT CTT AGC ATA CAA      1684
Thr Glu Asp Glu Arg Ile Gly Glu Asp Thr Pro Phe Leu Ser Ile Gln
            540             545                 550

AAT CCC ATG NCA ACC AGT CTG GAG CCA GCC TCT GCA TAT CGG CTG GCT      1732
Asn Pro Met Xaa Thr Ser Leu Glu Pro Ala Ser Ala Tyr Arg Leu Ala
555             560                 565                 570

GAG AAC AGG ACT AAC CCG NCA AAT CGC TTC TCC ACA CCA GAA GAG TTG      1780
Glu Asn Arg Thr Asn Pro Xaa Asn Arg Phe Ser Thr Pro Glu Glu Leu
            575             580                 585

CAA GCA AGG TTG TCC AGT GTA ATA GCT AAC CAA GAC CCT ATT GCT GTA      1828
Gln Ala Arg Leu Ser Ser Val Ile Ala Asn Gln Asp Pro Ile Ala Val
            590             595                 600

TAAGACATAA ACAAAACACA TAGATTCACA TGTAAAACTT TATTTTATAT AATGAAGTAT    1888

TCCACCTTTA AATTAAACAA TTTATTTTAT TTTAGCAATT CCGCTGATAG AAAACAAGAG    1948

TGGAAAAAGA AACTTTTATA AATTAAGTAT ACGTATGTAC AAATGTGTTA TGTGCCATAT    2008
```

FIGURE 1D

```
GTAGCAATTT TTTACAGTAT TTCCAAAATG GGGAAAGATA TCAATGGTGC CTTTATGTTA    2068

TGTTATGTTG AGAGCAAGTT TTGTACAGCT ACAATGATTG CTGTCCCGTA GTATTTTGCA    2128

AAACCTTCTA GCCCTCAGTT GTTCTGGCTT TTTTGTGCAT TGCATTATAA TGACTGGATG    2188

TATGATTTGC AAGAATTGCA GAAGTCCCCA TTTGCTTGTT GTGGAANCCC CAGATCAAAA    2248

AGCCCTGTTA TGGCACTCAC ACCCTATCCA CTTCACCAGG AAAAAAAAAA AATCAAAAAA    2308

AAAAAAAAAA AAAAAAGAA AAAAAAAAAA AAAAAGGAAT TCC                      2351
```

FIGURE 3

```
           C1                            C2                               C3                               C4  C5                          C6
ckARIA-1   L-T-K-C-D-I-K-Q-K-A-F-C-V-N-G-G-E-C-Y-M-V-K-D-L-P-N-P-P-R-Y-L-C-R-C-P-N-E-F-T-G-D-R-C-Q-N
ck/c-119   L-T-K-C-D-I-K-Q-K-A-F-C-V-N-G-G-E-C-Y-M-V-K-D-L-P-N-P-P-R-Y-L-C-R-stop
ck/c-124   L-T-K-C-D-I-K-Q-K-A-F-C-V-N-G-G-C-Y-M-V-K-D-L-P-s-P-P-R-Y-L-C-R-C-s-N-E-F-T-G-D-R-C-Q-N
ck/s-93    L-T-K-C-D-I-K-Q-K-A-F-C-V-N-G-g-C-Y-M-V-K-D-L-P-N-P-P-R-Y-L-C-R-stop
rtARIA-1   L-I-K-C-A-E-K-E-K-T-F-C-V-N-G-G-E-C-F-T-V-K-D-L-S-N-P-S-R-Y-L-C-K-C-P-N-E-F-T-G-D-R-C-Q-N HRG-β      L-V-K-C-A-E-K-E-K-T-F-C-V-N-G-G-E-C-F-M-V-K-D-L-S-N-P-S-R-Y-L-C-K-C-P-N-E-F-T-G-D-R-C-Q-N
NDF-β      L-I-K-C-A-E-K-E-K-T-F-C-V-N-G-G-E-C-F-T-V-K-D-L-S-N-P-S-R-Y-L-C-K-C-P-N-E-F-T-G-D-R-C-Q-N
HRG-α      L-V-K-C-A-E-K-E-K-T-F-C-V-N-G-G-E-C-F-M-V-K-D-L-S-N-P-S-R-Y-L-C-K-C-Q-P-G-F-T-G-A-R-C-T-E
NDF-α      L-V-K-C-A-E-K-E-K-T-F-C-V-N-G-G-E-C-F-T-V-K-D-L-S-N-P-S-R-Y-L-C-K-C-Q-P-G-F-T-G-A-R-C-T-E
HB-EGF     R-D-P-C-L-R-K-Y-K-D-F-C-I-H-*-G-E-C-K-Y-V-K-E-L-R-A-P-S-*-*-*-C-I-C-H-P-G-Y-H-G-E-R-C-H-G
AREG       K-N-P-C-N-A-E-F-Q-N-F-C-I-H-*-G-E-C-K-Y-I-E-H-L-*-*-*-E-A-V-T-C-K-C-Q-Q-E-Y-F-G-E-R-C-G-E
SDGF       K-N-P-C-A-A-K-*-Q-N-F-C-I-H-*-G-E-C-R-Y-I-E-N-L-*-*-*-E-V-V-T-C-H-C-H-Q-D-Y-F-G-E-R-C-G-E
EGF        D-S-E-C-P-L-S-H-D-G-Y-C-L-H-D-G-V-C-M-Y-I-E-A-L-*-*-*-D-K-Y-A-C-N-C-V-V-G-Y-I-G-E-R-C-Q-Y
TGF-α      F-N-D-C-P-D-S-H-T-Q-F-C-F-H-*-G-T-C-R-F-L-V-Q-E-*-*-*-D-K-P-A-C-V-C-H-S-G-Y-V-G-A-R-C-E-H
```

NEUROTROPHIC FACTOR

REFERENCE TO RELATED APPLICATIONS

This application is a continuation-in-part of U.S. Ser. No. 07/953,742, filed Sep. 29, 1992 and entitled "*Neurotrophic Factor*" now abandoned.

BACKGROUND OF THE INVENTION

The formation of functional contacts between developing axons and their targets is an essential step in the establishment of neuronal circuits. At the neuromuscular junction (nmj), as at other chemical synapses, the number and distribution of neuro-transmitter receptors are critical factors in determining the response to presynaptic stimulation. The neuromuscular junction is the best understood chemical synapse. Most of what is known about chemical synapses in the brain was either first or most completely analyzed at the nerve-muscle synapse. The transmitter at the nmj, acetylcholine (ACh) was identified more than 50 years ago. The ACh Receptor (AChR) was the first receptor/ion channel to be purified. It is composed of four subunits encoded by four different genes.

A cardinal event in the formation of the NMJ is the accumulation of acetylcholine receptors (AChRs) in the muscle membrane opposed to the nerve terminal. At the mature junction, receptors are packed in the postsynaptic membrane at a density in excess of 20,000 receptors/sq.micrometer. The localization is striking in that more than 70% of the receptors are concentrated to the motor endplate, a region that comprises less than 0.1 percent of the muscle-surface membrane.

Before the arrival of the motor nerve, nicotinic AChRs are distributed relatively uniformly over the surface of muscle fibers. The distribution of receptors can be mapped physiologically by measuring the sensitivity of the muscle membrane with an intracellular recording electrode while applying ACh ionphoretically from an extracellular microelectrode filled with 1M ACh and placed at different points over the muscle surface. The distribution of receptors can also be visualized using radiolabeled or fluorochrome labeled α-bungarotoxin (BgTx), a snake venom protein that binds selectively and almost irreversibly to nicotinic AChR (the type of AChR in skeletal muscle), or with monoclonal antibodies directed against extracellular regions of the receptor.

These labeling techniques reveal a dramatic change in the distribution of AChRs after innervation of the muscle fiber. There is a large increase in the density of receptors at the site of innervation and a decrease in the density of receptors at extrasynaptic sites. AChRs begin to accumulate at developing junctions within a few hours after nerve-muscle contact and the onset of synaptic transmission This phenomenon has been studied extensively in cell cultures containing embryonic motor neurons and myotubes. Individual synaptic partners can be visualized directly and monitored over periods of time that extend from seconds to several days.

Although a few AChRs and AChR clusters are present on uninnervated embryonic myotubes and myoblasts, it is clear that ingrowing motor nerves induce new receptor clusters rather than seeking out pre-existing ones (Anderson et al. 1977 *J. Physiol.* 268: 757; Frank and Fischbach 1979 *J. Cell Biol.* 83: 142). At least two processes contribute to the accumulation of AChRs at developing synaptic junctions. First, motor neurons may promote the aggregation of receptors that were present on the myocycte before nerve-muscle contact. These receptors may diffuse within the plane of the membrane and become immobilized at the synaptic site, presumably by binding to sites within the cytoskeleton and/or extracellular matrix. Second, motor neurons may induce the target muscle to increase the synthesis and insertion of new receptors in the immediate vicinity of the synapse. At chick synaptic junctions, the majority of AChRs at newly formed synapses or neurite associated receptor patches (NARPs) are newly inserted (Role et al., 1985 *J. Neurosci* 5:2197).

The motor nerve terminal triggers other changes in the properties of the postsynaptic receptor. For instance, AChRs at junctional sites lose their ability to diffuse in the plane of the membrane and gradually become fixed at the site of the synapse. Additionally, AChRs at junctional sites have a much longer half-life than extrajunctional receptors. AChRs found at newly formed end-plates in embryonic chicks have a half-life of about 24 hours, which is similar to that of extracellular receptors. With increasing time after synapse formation, junctional receptors become more stable, turning over with a half-life of more than 120 hours, whereas extrajunctional receptors are not stabilized.

The motor nerve also induces a change in the functional properties of nicotinic AChRs after skeletal muscle is innervated. AChR channels in embryonic rat muscle have a relatively small conductance (about 30pS) but remain open for long periods (about 5–10 mS) and have therefore been termed slow channels. In contrast, junctional receptors at mature end-plates have a significantly larger conductance (about 50pS) but remain open for a much shorter period (usually only about 1 mS) and are called fast channels.

AChRs at mature mammalian neuromuscular junctions are pentameric protein complexes composed of four subunits in the ratio of $\alpha_2\beta\epsilon\delta$ (Mishina et al. 1986 *Nature* 321: 406; Gu et al. 1988 *Neuron* 1:117, incorporated by reference herein). Most, if not all, embryonic AChRs contain a different subunit, termed "$\gamma$", in place of the $\epsilon$ subunit. When mixtures of $\alpha$, $\beta$, $\delta$, and $\gamma$ subunit mRNAs are injected into Xenopus oocytes, the expressed channels have the properties of embryonic receptors. When transcripts encoding the $\epsilon$-subunit are substituted for the $\gamma$ subunit, the resulting channels have the properties of adult receptors. It is likely that this change in subunit composition, which occurs during the first 2 weeks after birth and is due to a switch in gene expression, accounts for the switch in properties of ACh-activated channels from slow channels to fast channels which occurs over approximately the same time course.

The influence of the nerve on the AChR distribution appears to be mediated at least in part by difusable factors released by the presynaptic nerve terminal. For instance, myotubes located close to a spinal cord explant have been shown to be more sensitive to iontophoretically applied ACh and bind more $^{125}$I-BgTx than do myotubes located some distance away (Cohen and Fischbach, 1977 *Devel. Biol.* 59:24). Aceytlcholine itself does not seem to be the molecule responsible for the clustering of AChRs, as evidenced by the lack of AChR clustering in response to local application of ACh, and the observation that receptor clustering can occur when all AChRs are blocked by drugs such as curare.

Progress has been made in identifying a putative trophic factor that can increase the rate of receptor insertion, and that can promote the transition from embryonic to adult-type nicotinic AChRs. An Acetylcholine Receptor-Inducing Activity (ARIA) has been partially purified from adult chicken brains (Jessell et al., 1979 *PNAS* 76: 5397; Buc-Caron et al., 1983 *Div. Biol.* 95: 378; Usdin and Fischbach 1986 *J. Cell Biol* 103: 493). The purification was based on a sensitive assay in which the initial rate of appearance of new surface membrane AChRs are measured with $^{125}$I-BgTx four hours after blocking all exposed (old) receptors with unlabeled BgTx (Devreotes and Farobrough, 1975 *J. Cell Biol* 65: 335). The pitied protein was shown to increase the rate of AChR synthesis several fold with a $K_{app}$ in the picomolar range. ARIA does not appear to increase total protein synthesis or alter the degradation of surface receptors, but has been shown to affect the levels of certain AChR subunit mRNAs (Harris et al., 1988 *PNAS* 85: 7669).

This activity was shown to co-migrate with a protein that migrates as a broad band centered at an apparent MW of 42 kd by SDS-PAGE (Usdin et al. 1986 *J. Cell Biol.* 103:493). A chicken prion-like protein (Ch-PrLP) emerged as a major protein and apparently the only sequenceable protein in preparations of this activity (Falls et al. (1990) *Cold Spring Harbor Symp. Quant. Biol.* 55: 397). Based on N-terminal amino acid sequence analysis, oligonucleotides, were generated having sequences corresponding to portions of the chemically determined sequence of the protein present in the SDS-polyacrylamide band in which the activity was present, and were used to isolate a cDNA from an embryonic chick cDNA library. The isolated cDNA encodes a chicken protein that is homologous to the mammalian prion protein (PrPc). This chicken prion-like protein (ch-PrLP) was shown to be identical to the mouse PrP at 33% of its amino acid positions, and appeared to contain similar structural domains (Harris et al. 1991 *PNAS* 88: 7664, incorporated by reference herein).. However, the Ch-PrLP was not active when expressed, and anti-Ch-PrLP antibodies do not precipitate receptor-inducing activity.

SUMMARY OF THE INVENTION

The invention pertains to isolated neurotrophic factors, designated as ARIA, which are able to induce the formation of ion channels in a surface membrane of a cell. The amino acid sequence of the neurotrophic factors include an EGF-like domain, and a second amino acid sequence encoded by at least a portion of an exon of the neurotrophic factor gene expressible in a neuronal cell, especially a nerve cell. The neurotrophic factor is distinct from, and essentially unrelated to, the chicken prion-like protein previously identified.

The neurotrophic factors of the present invention have a spectrum of action which can include the induction of functional ion channel formation in a membrane of a cell. Examples of such ion channels include directly ligand-gated ion channels, such as acetylcholine receptors, glutamate receptors, GABA receptors and glycine receptors. For example, the neurotrophic factor can cause an increase in the number of nicotinic AChRs, and can effect an accumulation of the receptors in the surface membrane of a cell. Voltage-gated ion channels, such as the voltage-gated $Na^+$ channel, can also be affected by ARIA treatment. The neurotrophic factor can also induces functional ion channel formation of indirectly ligand-gated ion channels, such as muscarinic acetylcholine receptors. For example the neurotrophic factor of the present invention can increase the number of functional G-protein coupled receptors.

In one embodiment of the invention, the amino acid sequence of one variant of the neurotrophic factor is shown in FIG. 1 (SEQ. ID Nos. 1 and 2). In other embodiments, the amino acid sequence of particular variants of ARIA are given by SEQ. ID Nos. 4, 32, 33, 35 and 37. ARIA can be isolated as a full length protein, including the transmembrane and cytoplasmic domains. However, functional ARIA fragments will comprise the EGF-like domain, and will lack the transmembrane and cytoplasmic domains if soluble.

The factor can be produced by isolating it in its native form from cells or tissue that produce the factor, such as brain tissue, by chemical synthesis, or by recombinant DNA techniques.

This invention additionally pertains to isolated nucleic acid (DNA or RNA) encoding the neurotrophic factor, to cloning or expression vectors containing the nucleic acid, and to cells transformed with these vectors. Another aspect of the invention is direct to antibodies, including monoclonal and polyclonal antibodies, which are directed against the neurotrophic factor.

The neurotrophic factor of this invention, and related proteins having an EGF-like amino acid sequences, such as heregulins and neu differentiation factor (NDF), can be used as either agonists or antagonists, to influence the formation of functional ion channels, such as acetylcholine receptors, in the surface membrane of a postsynaptic cell.

BRIEF DESCRIPTION OF THE DRAWINGS

FIGS. 1A–D represent the nucleotide (SEQ. ID NO. 1) and amino acid (SEQ. ID NO. 2) sequence of ARIA cloned from a chicken brain cDNA library. The sequences bounded by the numbered brackets are as follows, (1) Nex1 (SEQ ID NO:24), (2) Ig-like domain, (3) Nex2 (SEQ ID NO:20), (4) EGF-like domain (SEQ ID NO:22), (5) transmembrane domain. Amino acid sequences located C-terminal to the transmembrane domain correspond to the cytoplasmic portion of ARIA, while those amino acid sequences N-terminal to the transmembrane domain are the extracellular portion. Nex1 roughly comprises amino acid residues 1–27, the Ig-like domain comprises residues 45–108, Nex2 roughly comprises amino acid residues 116–127, the EGF-like domain comprises residues 141–180, the transmembrane domain comprises amino acid residues 207–229.

FIG. 3 is an alignment of the EGF-like amino acid sequences of distinct ARIA variants cloned from chicken (SEQ ID NOS. 1, 27, 28 and 29) and rat (SEQ ID NO. 33), with the EGF-like domains of Heregulin-β and -α (SEQ ID NOS. 37 and 39), Neu Differentiation Factor-β and -α (SEQ ID NOS. 38 and 40), Heparin-binding EGF-like growth factor (SEQ ID NO. 41), amphiregulin (SEQ ID NO. 42), Schwanoma-derived growth factor (SEQ ID NO. 43), Epitheleal Growth Factor (SEQ ID NO. 44), and Tumor Nercrosis Factor (SEQ ID NO. 45).

DETAILED DESCRIPTION OF THE INVENTION

Figure 2:
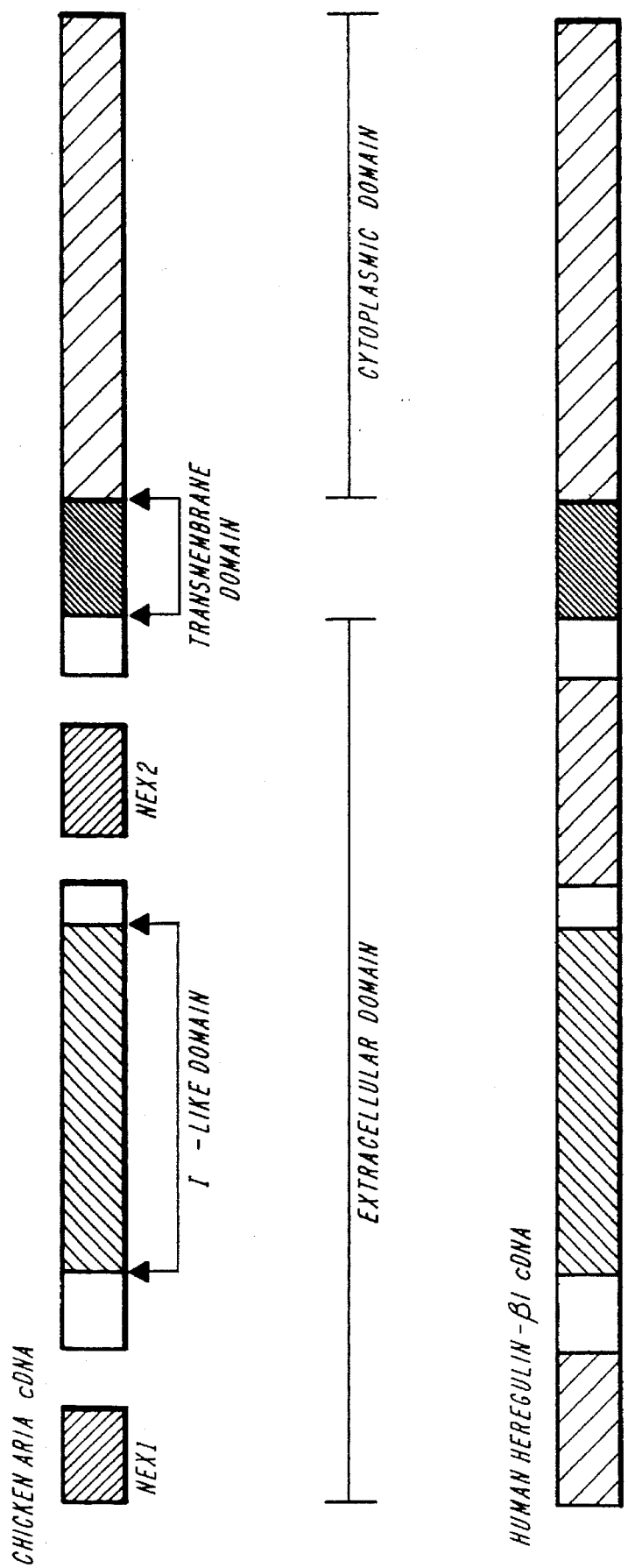
FIG. 2 is a schematic representation of the structural domains and motifs of ARIA corresponding to the amino acid sequence of FIGS. 1A–D.

An Acetylcholine Receptor Inducing Activity (ARIA) was previously shown to co-purify from chicken brain extracts, through a number of chromatographic steps, with a protein that migrates as a broad band centered at MW 42,000 in SDS-polyacrylamide gels (Usdin et al. 1986 *J. Cell Biol.* 103:493). A chicken prion-like protein was cloned and identified by screening a chicken brain cDNA library with oligonucleotides derived from the chemically determined sequence of the only apparently sequenceable protein in the purified preparations of ARIA (Harris et al. 1991 *PNAS* 88:7664).

As described herein, a neurotrophic factor, termed ARIA, has been isolated and cloned on the basis of its ability to promote the synthesis and accumulation of AChRs in cultured muscle cells. In one aspect of the invention, purification of endogenous ARIA from chicken brain extracts was accomplished by a series of reverse-phase, ion exchange, and size exclusion chromatography steps. Most recently, we have discovered that ARIA is retained on a heparin column under conditions that do not support the binding of ch-PrLP. Partial amino acid sequencing of tryptic fractions prepared from the heparin-purified ARIA has allowed cloning of the protein from a chicken cDNA library. The nucleotide sequence, and the corresponding amino acid sequence, of the neurotrophic factor cloned from the messenger library is shown in FIG. 1. The heparin-purified ARIA protein from chicken brain is believed to be contained within the extracellular domain of this large transmembrane precursor neurotrophic factor. The amino acid sequence of ARIA is entirely distinct from the ch-PrLP previously identified in ARIA-containing chromatographic fractions. As described below, an ARIA homolog has also been cloned from rat, and shares a many domain features with the chicken clone.

The cloned cDNA has been expressed in cultured mammalian cells, and can induce an increase in AChR levels in cultured muscle cells. The cloned cDNA that encodes ARIA has been transfected into COS-7 cells, and medium conditioned by the transformed cells stimulates the synthesis of AChRs in skeletal muscle cells. The significant increase in AChR levels indicate that the protein corresponding to the cloned cDNA is in fact ARIA.

In cells treated with ARIA, there is not any significant increase in total protein synthesis; rather, ARIA selectively affects the synthesis and/or the number of functional ion channel receptors, or the of molecules that are concentrated at synapses and generally present in low abundance elsewhere on the cellular membrane. For instance, both the cloned and purified endogenous forms of ARIA can induce an increase in the number of nicotinic acetylcholine receptors in the surface membrane of a cell. The addition of ARIA to either cultured chicken, rat, human or mouse myotubes has been demonstrated to result in an increase in the appearance of new α-BgTX binding sites in the myotube cultures.

In addition to nicotinic AChRs of the nmj, the spectrum of action of ARIA is likely to include the regulation of a wide range of ion channels and other molecules concentrated at chemical synapses. For example, ion channels affected by ARIA can include members of the super-family of ligand-gated ion channels (see Betz 1990 *Neuron* 5:383, incorporated herein by reference) including neuronal nicotinic AChRs. For instance, partially purified ARIA increases the response of ciliary ganglion neurons to ACh. Highly purified ARIA phosphorylates a 185 kD protein in ciliary ganglion neurons, which as discussed below, is highly correlated with AChR synthesis. These cells are models for neurons in the brain that exhibit nicotinic AChRs, as they contain similar subunits. Other neurotransmitter receptors of the central nervous system (CNS) such as amino acid receptors for gamma-amino butyric acid (GABA), glycine, and glutamate, which form ligand-gated ion channels having similar organizational and significant amino acid identity with the subunits of the nicotinic AChRs can be affected by ARIA. GABA and glycine receptors are concentrated beneath inhibitory boutons on central neurons, and glutamate receptors are concentrated at neurite contacts, presumably excitatory synapses.

Another example of an ion channel likely to be affected by treatment with ARIA is the voltage-gated $Na^+$ channel, which also shares similar structural motifs with the ligand-gated family of ion channels. This effect is suggested by the observation that ARIA can increase the saxitoxin (STX) binding (two fold) and peak inward $Na^+$ currents in cultured muscle cells (see Falls et al. 1990 *Cold Spring Harbor Symp. Quant. Biol.* 55:397). Similarly, other voltage-gated ion channels, including $Ca^{++}$ channels and $K^+$ channels, can be affected by ARIA because they are structurally related to $Na^+$ channels.

Also, ARIA can affect ion channels activated indirectly via G-protein coupled chemoreceptors, such as muscarinic AChRs. This action of ARIA is supported by the observation that ARIA-containing brain extract increases the ACh response of ventricular cardiac muscle cells (see Siegel et al. 1984 *Develop. Biol.* 101:346, incorporated herein by reference), and the response is due to activation of muscarinic AChRs.

Thus, the term "ion channels" as used herein is meant to include voltage-gated, directly ligand-gated, and indirectly ligand-gated ion channels.

There presently exists a battery of reagents which are specific for a wide range of ion channels, and will allow the determination of the levels of functional ion channels in the presence and absence of ARIA. Thus, the effect of the neurotrophic factor of the present invention on a particular ion channel can be easily assessed.

Consistent with this understanding that ARIA can be a multifunctional protein whose biological activities may be context dependent, we have studied the expression of ARIA mRNA in the nervous system by in situ hybridization using anti-sense RNA probes to the ARIA gene sequences described herein, and have found a pattern of expression indicative of a role for ARIA inclusive of each class of ion channel set out above.

In the rat brain, to illustrate, ARIA mRNA is present in many cholinergic neurons in the brain stem and cerebral hemispheres. In particular, ARIA mRNA was found in motor nuclei of the III, IV, V, VII, IX and X cranial nerves. In the hemispheres it is abundant in the septal nuclei and the diagonal band of Broca. These observations further support the assertion that ARIA regulates ACh receptors in the cerebral cortex (neocortex and hippocampus), and hence may enhance the formation and recall of memory.

ARIA mRNA is also present in non-cholinergic neurons in the brain. For example, the present ARIA mRNA probes detected ARIA message in cells of the pontine nuclei, other thalamic and midbrain nuclei, and granule cells of the cerebellum. These findings are consistent with a role for ARIA in effecting other ion channels. We have also studied the distribution of ARIA mRNA expression in the chick using a probe to the 5' end of a chicken ARIA cDNA. The results are similar to those found in the rat. We have found that some cholinergic and some non-cholinergic neurons contain ARIA mRNA, many of them being the homologous structures to the ones labeled in the rat brain.

Furthermore, ARIA expression is not limited to neural tissue. In both rat and chick tissue samples, ARIA mRNA level is very high in the endocardium, a monolayer of endothelial cells covering the heart's chambers. In the embryo, the endocardial cells constitute the earliest formed structures of the heart, around which the myocardium then proliferates, and from which the heart's valves are formed. While the function of the endocardium is still in question, it has been proposed that it constitutes an important modulator of the performance of the subjacent myocardium (Brutsaert, (1989) *Annual Rev. Physiol.* 51:263–273). It is conceivable that ARIA produced by the endocardium plays a role in the proliferation and differentiation of the heart muscles as well as in the modulation of its electrical and mechanical properties. This is further supported by the observation that p185

(discussed below) is phosphorylated in myocytes from E5 chick embryos in response to treatment with ARIA.

Indeed, labeling studies in chick brain samples during various stages of development tend to support the concept of a broader involvement for ARIA in biological function beyond just ion channel induction, which can include mitogenic as well as growth factor-like activities. For example, ARIA mRNA is present in proliferating neuronal populations. This is most clear in the cerebellar granule cells, which express ARIA mRNA while located in the External Granule Cell Layer, where they undergo cell division. They continue to express ARIA mRNA immediately after migrating to the Internal Granule Cell Layer, the position that they will retain in the adult brain.

The present invention makes available isolated ARIA which is substantially free of prion-like protein and recombinant ARIA produced by the expression of the cloned ARIA gene or a fragment thereof. The term "substantially free of prion-like protein" is defined herein as encompassing ARIA preparations comprising less than 20% (by dry weight) prion-like protein, and preferably comprises less than 5% prion-like protein. Functional forms of ARIA can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other trophic factors, as well as priori-like proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. The term "isolated" as used herein refers to a peptide, DNA, or RNA molecule separated from other peptides, DNAs, or RNAs, respectively, that are present in the natural source of the macromolecule. "Isolated" and "purified" do not encompass either natural materials in their native state or natural materials that have been separated into components (e.g., in an acrylamide gel) but not obtained either as pure (e.g. lacking prion-like proteins) substances or solutions.

ARIA can be used to supplement cell culture media for growth of postsynaptic target cells (e.g. muscle or nerve cells), and provide a means for examining changes in ion channel states, which may ordinarily require complex procedures for co-culturing of several nerve cells-types. For instance, the neurotrophic factor, or an active fragment thereof, can cause an increase in synthesis of nicotinic AChRs, and can effect an accumulation of the receptors in the surface membrane of a cell. The neurotrophic factor can regulate a phenotypic change in nicotinic AChRs from slow to fast channels, as well as increase the level of mRNA encoding the $\alpha$- and $\epsilon$-subunits of the receptor. Thus, augmentation of the culture medium with the neurotrophic factor of this invention can allow further definition of the events triggered by innervation.

The neurotrophic factor of the present invention can be used to produce anti-ARIA antibodies using known techniques. Both monoclonal and polyclonal antibodies (Ab) directed against ARIA, and antibody fragments such as Fab and $F(ab)_2$, can be used to block the action of ARIA and allow the study of the formation of neurite-associated receptor patches (NARPS) at developing nerve-muscle and nerve-nerve synapses in the absence, or controlled presence, of ARIA. For instance, such studies can be carried out in nerve and muscle cell co-cultures.

The effect of anti-ARIA Abs on NARP formation can also be assayed in vivo, such as in intact embryos. For instance, purified monoclonal Abs can be injected directly into the limb buds of E5 chick embryos. It has been demonstrated that the motor axons enter the limb bud on E4.5, and the first clusters of AChRs are detectable with $\alpha$-BgTx late in E5. Thus, the use of anti-ARIA Abs during this developmental stage can allow assessment of the effect of ARIA on the formation of neuron-muscle synapses in vivo. In a similar approach, hybridomas producing anti-ARIA monoclonal Abs, or biodegradable gels in which anti-ARIA Abs are suspended, can be implanted at a site proximal or within the area at which ARIA action is intended to be blocked. Experiments of this nature can aid in deciphering the role of other factors that may be involved in NARP formation.

Antibodies which specifically bind ARIA epitopes can also be used in immunohistochemical staining of tissue samples in order to evaluate the abundance and pattern of expression of ARIA and ARIA homologs. Anti-ARIA antibodies can be used diagnostically in immuno-precipitation and immuno-blotting to detect and evaluate ARIA levels in tissue or bodily fluid as part of a clinical testing procedure. For instance, such measurements can be useful in predictive valuations of the onset or progression of neurological disorders, such as those marked by denervation-like or disuse-like symptoms, or where there is reason to believe that there is a deficiency in ion channels. Likewise, the ability to monitor ARIA levels in an individual can allow determination of the efficacy of a given treatment regimen for an individual afflicted with such a disorder. The level of ARIA can be measured in bodily fluid, such as in samples of cerebral spinal fluid, or can be measured in tissue, such as produced by biopsy. Diagnostic assays using anti-ARIA antibodies can include immunoassays to aid in early diagnosis of Alzheimer's disease, as a decrease in nicotinic AChRs in the cerebral cortex occurs in this dementing disorder. Other immunoassays involving anti-ARIA antibodies may include tests for diagnosing early stages of myasthenia gravis, and amyotrophic lateral sclerosis.

Another application of anti-ARIA antibodies is in the immunological screening of cDNA libraries constructed in expression vectors such as $\lambda$gt11, $\lambda$gt18–23, $\lambda$ZAP, and $\lambda$ORF8. Messenger libraries of this type, having coding sequences inserted in the correct reading frame and orientation, can produce fusion proteins. For instance, $\lambda$gt11 will produce fusion proteins whose amino termini consist of $\beta$-galactosidase amino acid sequences and whose carboxy termini consist of a foreign polypeptide. Antigenic epitopes of ARIA can then be detected with antibodies, as for example reacting nitrocellulose filters lifted from infected plates with anti-ARIA antibodies. Phage, scored by this assay, can then be isolated from the infected plate. Thus, the presence of ARIA and ARIA homologs can be detected and cloned from other sources. The fact that ARIA from either chicken or rat will induce AChR insertion in myotubes of other species, including human, suggests a certain homology must exist between the homologs of ARIA from evolutionarily diverse sources. Thus, screening a human fusion protein library with an anti-ARIA antibody raised against ARIA from a non-human species can also allow the cloning of a human ARIA.

The nucleotide sequence determined from the cloning of ARIA from both chicken and rat will further allow for the generation of probes designed for use in identifying ARIA homologs in other animals, especially humans. For instance, as described in Example Seven, such probes can be used, in known methods, to screen both messenger and genomic DNA libraries for the presence of homologous sequences ostensibly arising from an ARIA-like gene encoding an ARIA homolog. As above, each technique can facilitate the cloning of a human homolog of ARIA.

In addition, nucleotide probes can be generated, as described in Example Nine, from the cloned sequence of ARIA, which allow for histological screening of intact tissue and tissue samples for the presence of ARIA mRNA. Similar to the diagnostic uses of anti-ARIA antibodies, the use of probes directed to ARIA mRNA, or to genomic ARIA sequences, can be used for both predictive and therapeutic evaluation of neurological disorders. Used in conjunction with anti-ARIA antibody immunoassays, the nucleotide probes can help facilitate the determination of the molecular basis for a neurological disorder which may involve some abnormality associated with ARIA. For instance, variation in ARIA synthesis can be differentiated from a change in ARIA metabolism (such as increased catabolism).

Also, similar to the antibody blocking experiments, the use of anti-sense techniques (e.g. microinjection of antisense molecules, or transfection with plasmids whose transcripts are anti-sense with regard to ARIA mRNA) can be used to study synapse formation in a controlled ARIA environment by inhibiting endogenous ARIA production. Such techniques can be utilized in cell culture, but can also be used in the creation of transgenic animals.

The neurotrophic factor described herein can be used to treat (prevent and/or reduce the severity of) a number of neurological disorders in which modulation of ion channel levels or ion channel activity can be of therapeutic value. The term "neurological disorders" includes diseased or abnormal states in an individual which can include degenerative growth and development disorders, as well as degenerative diseases. Such neurological disorders can affect the central nervous system or the peripheral nervous system, or both. Also included are altered memory and decline in cognitive functions, as for example, resulting from normal aging processes. Neurological disorders which may be amenable to treatment with ARIA agonists or antagonists may also include any disease where levels of ARIA metabolism are altered and therefor ion channel levels or activity are abnormal.

Examples of neurological disorders which may be treatable with ARIA include Alzheimer's disease, myasthenia gravis, and dementias associated with diseases such as Huntington's disease and Parkinson's disease.

Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies.

ARIA can also be used in the treatment of autonomic disorders of the peripheral nervous system, which include disorders affecting the innervation of smooth muscle and endocrine tissue (such as glandular tissue). For instance, tachycardia is usually associated with an abnormally low level or activity of muscarinic AChRs in the striated muscle of the heart and may be treatable with an ARIA agonist. Likewise, atrial cardiac arrythmias are also influenced by the activity of the muscarinic AChRs of the heart. Hypertension may be treatable with ARIA antagonists, for instance, by controlling the sensitivity of the sympathetic nervous system to stimulation, or in treating individuals in which abnormalities exist at baroreceptor connections or within the tractus oblongata.

ARIA may also be useful as a memory enhancer, especially in young and old subjects. Atropine and scopolamine, which block muscarinic AChR, result in memory loss. Cholinomimetrics (which may activate nicotinic as well as muscarinic receptors) enhance memory performance in all age groups. Thus, by increasing ion channel levels, ARIA can act to enhance memory and cognitive functions Also, nicotine itself is a cognitive enhancer. ARIA, by increasing the number of nicotinic receptors, may eliminate the "craving" for nicotine.

In the treatment of such diseases, it may be desirable to administer an ARIA agonist in circumstances where an increase in the level of functional ion channels at a chemical synapse are desired. "Agonist" refers to ARIA, a suitable homolog, or an ARIA or ARIA homolog peptide, capable of promoting at least one of the biological responses normally associated with ARIA. For example, partial proteolytic digestion of ARIA results in smaller peptides, some of which are capable of inducing nicotinic AChR synthesis. Thus, fragments of ARIA may serve as ARIA agonists. The heregulins, NDF and portions thereof, as well as other EGF-like proteins or EGF-like domains, may also be suitable agonists.

In other instances, it may be desirable to administer ARIA antagonists, such as a mutant form of ARIA or an ARIA homolog which blocks at least one of the normal actions of ARIA. Such strategies may be part of treating neurological disorders made manifest by an increased activation of ion channels, such as epilepsy. Thus, treatment with ARIA antagonists can down-regulate the ion channels. In the presence of an ARIA antagonist, ARIA has reduced ability to mediate biological responses normally associated with ARIA. Similar to the use of ARIA antagonists, anti-ARIA antibodies can be used to decrease levels of functional ion channel.

The present invention, by making available purified and recombinant ARIA, will allow the development of assays which can be used to screen for drugs which are either agonists or antagonists. By mutagenesis, and other structural surveys of the neurotrophic factor, rationale drug design can be employed to manipulate ARIA or portions thereof, as either agonists or antagonists, as well as facilitate design of small molecule agonists and antagonists.

A nucleotide sequence derived from the cloning of ARIA, encoding all or a selected portion of the protein, can be used to produce a recombinant form of ARIA via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known promins, e.g. insulin, interferons, human growth hormone, IL-1, IL-2, and the like. Similar procedures, or obvious modifications thereof, can be employed to prepare recombinant ARIA, or portions thereof, by microbial means or tissue-culture technology in accord with the subject invention.

The recombinant ARIA protein can be produced by ligating the cloned gene, or a portion thereof, into a vector suitable for expression in either prokaryotic cells, eukaryotic cells, or both. Expression vehicles for production of recombinant ARIA include plasmids and other vectors. For instance, suitable vectors for the expression of ARIA include plasmids of the types: pBR322-derived plasmids, pEMBL-derived plasmids, pEX-derived plasmids, pBTac-derived plasmids and pUG-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see for example Broach et al. (1983) in Experimental Manipulation of Gene Expression, ed M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures, see Molecular Cloning A Laboratory Manual, 2nd Ed., ed. by Sambrook, Fritsch and Maniatis (Cold Spring Harbor Laboratory Press:1989) Chapters 16 and 17, incorporated by reference herein.

In some instances, it may be desirable to express the recombinant ARIA by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the g-gal containing pBlueBac III).

Depending in the expression system chosen, the ability to obtain a recombinant protein which is either glycosylated or not can be controlled.

When expression of a portion of ARIA is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing ARIA-derived polypeptides in a host which produces MAP (e.g., E. coli or CM89 or S. Cerevisiae), or in vitro by use of purified MPA (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of ARIA. For example, the VP6 capsid protein of rotavirus can be used as an immunologic carrier protein for portions of the ARIA polypeptide, either in the monomeric form or in the form of a viral particle. The nucleic acid sequences corresponding to the portion of ARIA to which antibodies are to be raised can be incorporated into a fusion gene construct which includes coding sequences for a late vaccinia virus structural protein to produce a set of recombinant viruses expressing fusion proteins comprising a portion of ARIA as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of ARIA and the poliovirus capsid protein can be created to enhance immunogenecity of the set of polypeptide antigens (see for example EP Publication No. 0259149; and Evans et al. (1989) Nature 339:385; Huang et al. (1988) J. Virol. 62:3855; and Schlienger et al. (1992) J. Virol. 66:2, incorporated by reference herein).

The Multiple Antigen Peptide (MAP) system for peptide-based immunization can be utilized, wherein a desired portion of ARIA is obtained directly from organo-chemical synthesis of the peptide onto an oligomeric branching lysine core (see for example Posnett et al. (1988) JBC 263:1719 and Nardelli et al. (1992) J. Immunol. 148:914, incorporated by reference herein). Antigenic determinants of ARIA can also be expressed and presented by bacterial cells.

In addition to utilizing fusion proteins to enhance immunogenicity, it is widely appreciated that fusion proteins can also facilitate the expression of proteins, such as ARIA, by the use of secretory-directing signal peptides (e.g., see Achstetter et al. 1992 Gene 110:25).

In another common use of fusion proteins, a fusion gene can be created having additional sequences coding for a polypeptide portion of the fusion protein which will facilitate its purification. For example, a fusion gene coding for a purification leader sequence, such as a poly-(His)/enterokinase cleavage site sequence, at the N-terminus of the desired portion of ARIA can allow purification of the expressed ARIA fusion protein by affinity chromatography using a $Ni^{2+}$ metal resin. The purification leader sequence can then be subsequently removed by treatment with enterokinase (e.g., see Hochuli et al. 1987 J. Chromatography 411:177; and Janknecht et al. PNAS 88:8972, incorporated by reference herein).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the fusion gene can be synthesized by conventional techniques including automated DNA synthesizers.

Moreover, variations of the ARIA peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur -containing=cysteine and methoinine. (see, for example, *Biochemistry*, 2nd ed, Ed. by L. Stryer, WH Freeman and Co.:1981). Whether a change in the amino acid sequence of a peptide results in a functional ARIA homolog can be readily determined by assessing the ability of the variant peptide to produce a response in cells in a fashion similar to the wild-type ARIA. Peptides in which more than one replacement has taken place can readily be tested in the same manner.

It has been recently reported that a 45 kD protein heregulin-α (HRG-α) has been cloned from an mRNA-derived MDA-MB231 cell library. In addition, several complementary DNA clones encoding related HRGs were also identified, all the HRGs being similar to some extent to proteins in the epidermal growth factor (EGF) family (Holmes et al. 1992 *Nature* 256: 1205, incorporated by reference herein).

It has also been reported that a 44 kD glycoprotein secreted by transformed rat fibroblasts, termed Neu differentiation factor (NDF), has been cloned and expressed (Wen et at. 1992 *Cell* 69:559, incorporated by reference herein).

The amino acid sequence of the cloned neurotrophic factor ARIA demonstrates a high degree of sequence homology with both rat NDF and the heregulins, especially heregulin-β1. The form of the neurotrophic factor isolated from chicken brain appears to exist in vivo as a glycoprotein, and has an apparent molecular weight in the range of 40 kd to 45 kd when electrophoretically chromatographed on a 13% SDS-polyacrylamide gel. Similar to rat NDF and human heregulins, ARIA identified in both chicken and rat possess an immunoglobulin-like domain as well as an EGF-like domain. However, ARIA also contains two stretches of amino acid residues in the amino terminal half of the extracellular domain, referred to herein as Nex-1 and Nex-2, which can be divergent in sequence from the corresponding amino acid positions in rat NDF and the human heregulins, as well as other growth factors and mitogens including SDGF and the Glial Growth Factors.

As described in Examples Seven and Eight, using probes directed to nucleotide sequences determined in either the chicken ARIA clone or the rat NDF clone, rat spinal cord mRNA was reverse transcribed and the cDNA amplified by PCR. In one instance, a 230 bp fragment was amplified and cloned into a bacterial fusion expression system. The sequence of the PCR fragment indicated substantial homology with ARIA purified from chicken as well as heregulin-β1. This fragment, which corresponds to the EGF-like amino acid sequence of chicken ARIA, has been expressed, isolated, and applied to muscle cell cultures. This rat ARIA fragment causes phosphorylation of p185, as observed with ARIA isolated from chicken brain. While the EGF-like domain of rat ARIA is closely homologous in sequence to heregulin-β, consistent with the above assertion rat ARIA appears to be divergent in sequence from rat NDF and the heregulins at nucleotide positions roughly corresponding to Nex-1 and Nex-2 of the chicken ARIA (though one rat ARIA clone is identical at Nex-2 to HRG-β). Evidence supporting this observation includes the demonstration of the lack of ability of PCR primers, based on 5' sequences of NDF or heregulin, to amplify sequences (especially 5' to the nucleotides encoding the Ig-like domain), in conjunction with 3' probes that have been shown to bind appropriately to rat ARIA in other reactions, indicating that the 5' sequences of rat NDF and heregulin messages are not present in spinal cord.

Thus, the neurotrophic factors of this invention contain an EGF-like amino acid sequence and an amino acid sequence encoded by at least a portion of an exon of the neurotrophic factor gene expressed in a neuronal cell, preferably a nerve cell. The factors can also contain an immunoglobulin-like domain, a transmembrane domain and a cytoplasmic domain. The biological activity of the factor with respect to inducing the synthesis of functional ion channels is believed to require the EGF-like domain of the protein. The overall "domain" structure of ARIA cloned from chicken is shown in FIG. 2, and the domain structure of the various rat clones is consistent with this depiction.

The cysteinyl-bounded core amino acid sequence of the EGF family of mitogens has the consensus sequence $CY_1CY_2CY_3CY_4CY_5C$, where C is a cysteine, $Y_1$ represents 7 amino acids which can be the same or different, $Y_2$ represents 4 to 5 amino acids which can be the same or different, $Y_3$ represents 10 to 13 amino acids which can be the same or different, $Y_4$ represents any amino acid, and $Y_5$ represents 8 amino acids which can be the same or different, and is generally 36–40 residues in length. Based on this general arrangement of cysteine residues, a closely related motif, termed EGF-like motif, has been identified in a number of proteins. As used herein, an EGF-like amino acid sequence is a sequence which exhibits the EGF-like motif as represented by the general formula $CX_1CX_2CX_3CX_4CX_5C$, where C is a cysteine, $X_1$ represents 4 to 14 amino acids which can be the same or different, $X_2$ represents 3 to 8 amino acids which can be the same or different, $X_3$ represents 4 to 14 amino acids which can be the same or different, $X_4$ is any amino acid, and $X_5$ represents 8 to 14 amino acids which can be the same or different. Examples of EGF-like amino acid sequences are given in SEQ ID NOS. 2, 4, and 26–43)

Amino acid sequences expressed in neuronal cells include the Nex-1 and Nex-2 amino acid sequences, which as stated above, can be highly divergent in sequence relative to NDF and the heregulins. It is likely that Nex-1 and Nex-2 arise by way of differential splicing. As is illustrated by the diversity of ARIA homologs Cloned from both chicken and rat, within a population of cells of the nervous system, other exons may be substituted in other ARIA homologs.

This invention further contemplates a method of generating sets of combinatorial mutants of ARIA, and is especially useful for identifying potential variant sequences (e.g. homologs) that are functional in binding to a receptor for ARIA. The purpose of screening such combinatorial libraries is to generate, for example, novel ARIA homologs which can act as either agonists or antagonist, or alternaitvely, possess novel activities all together. To illustrate, novel EGF-like domains (e.g. those not naturally occurring in ARIA) can be engineered by the present method to provide more efficient binding to an ARIA receptor yet still retain at least a portion of an activity associated with an ARIA. Thus, combinatorially-derived homologs can be generated to have an increased potency relative to a naturally occurring ARIA. Likewise, ARIA homologs can be generated by the present combinatorial approach to act as antagonists, in that they are able to bind an ARIA receptor yet not induce any biological response, thereby blocking the action of ARIA or an ARIA agonist. Moreover, manipulation of certain domains of ARIA by the present method can provide domains more suitable for use in fusion proteins, such as one that incorporates portions of other proteins which are derived from the extracellular matrix and/or which bind extracellular matrix components.

As described herein, ARIA has been cloned from several sources, including chicken and rat, and ARIA from either species has been shown to be active in inducing ion channel formation in human myotubes. Moreover, as described above, cDNA-derived amino acid sequences have become available for other apparent trophic factors that are sufficiently similar to indicate common ancestry with ARIA. These related proteins have a similar domain structure including an EGF-like domain and an Immunoglobulin-like domain. Interestingly, variants of ARIA were cloned from chicken mRNA derived from both spinal cord and cerebellum mRNA libraries that included a stop codon positioned in place of the C5 cyteine of the EGF-like domain (SEQ ID NOS. 27 and 29), giving rise to truncated ARIA porteins. While the role of such truncation variants of ARIA is not known, such mutations may give rise to antagonistic variants of ARIA.

In one aspect of this method, the amino acid sequences for a population of ARIA variants or other related proteins are aligned, preferably to promote the highest homology possible. Such a population of variants can include, for example, naturally occurring ARIA and ARIA homologs from one or more species, as well as amino acid sequences of other proteins, such as those derived from the heregulin family, which are known to, or expected to, possess some ability to induce ARIA-like responses in cells. Amino acids which appear at each position of the aligned sequences are selected to create a degenerate set of combinatorial sequences.

In a preferred embodiment, the combinatorial ARIA library is produced by way of a degenerate library of genes encoding a library of polypeptides which each include at least a portion of potential ARIA sequences. A mixture of synthetic oligonucleotides can be enzymatically ligated into gene sequences such that the degenerate set of potential ARIA sequences are expressible as individual polypeptides (such as discrete EGF-like domains), or as a set of larger fusion proteins containing the set of ARIA sequences therein.

As illustrated in FIG. 3, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, FIG. 3 includes the alignment of several EGF-like domains of various cloned forms of ARIA from different species. The sequences are aligned by the conserved cysteine residues present in each variant. Analysis of the alignment of only the EGF-like domains of the ARIA clones shown in FIG. 3 can give rise to the generation of a degenerate library of polypeptides comprising potential EGF-like sequences represented by the general formula (SEQ ID NO:46):

Cys-Xaa(1)-Xaa(2)-Lys-Xaa(3)-Lys-Xaa(4)-Phe-Cys-Val-Asn-Gly-
Gly-Xaa(5)-Cys-Xaa(6)-Xaa(7)-Val-Lys-Asp-Lys-Xaa(8)-
Xaa(9)-Pro-Xaa(10)-Arg-Tyr-Leu-Cys-Xaa(11)-Cys-Xaa(12)-
Asn-Glu-Phe-Thr-Gly-Asp-Arg-Cys or,

Cys-Xaa(1)-Xaa(2)-Lys-Xaa(3)-Lys-Xaa(4)-Phe-Cys-Val-Asn-Gly-
Gly-Xaa(5)-Cys-Xaa(6)-Xaa(7)-Val-Lys-Asp-Lys-Xaa(8)-
Xaa(9)-Pro-Xaa(10)-Arg-Tyr-Leu-Cys-Xaa(11)

wherein Xaa(1) is an Asp, or Ala; Xaa(2) is an Ile, or Glu; Xaa(3) is a Gln, or Glu; Xaa(4) is an Ala, or Thr; Xaa(5) is a Glu, or Gly; Xaa(6) is a Tyr, or Phe; Xaa(7) is a Met, or Thr; Xaa(8) is a Pro, or Ser; Xaa(9) is an Asn, or Ser; Xaa(10) is a Pro, or Ser; Xaa(11) is an Arg, or Lys; Xaa(12) is a Pro, or Ser.

Further expansion of the combinatorial library can be made, for example, by including amino acids which would represent conservative mutations at one or more of the degenerative positions of the aligned variants. Inclusion of such conservative mutations can give rise to a library of potential ion channel-inducing activities represented by the formula (SEQ ID NO:46):

Cys-Xaa(1)-Xaa(2)-Lys-Xaa(3)-Lys-Xaa(4)-Phe-Cys-Val-Asn-Gly-
Gly-Xaa(5)-Cys-Xaa(6)-Xaa(7)-Val-Lys-Asp-Lys-Xaa(8)-
Xaa(9)-Pro-Xaa(10)-Arg-Tyr-Leu-Cys-Xaa(11)-Cys-Xaa(12)-
Asn-Glu-Phe-Thr-Gly-Asp-Arg-Cys or,

Cys-Xaa(1)-Xaa(2)-Lys-Xaa(3)-Lys-Xaa(4)-Phe-Cys-Val-Asn-Gly-
Gly-Xaa(5)-Cys-Xaa(6)-Xaa(7)-Val-Lys-Asp-Lys-Xaa(8)-
Xaa(9)-Pro-Xaa(10)-Arg-Tyr-Leu-Cys-Xaa(11)

wherein Xaa(1) is an Asp, Ala, Glu, Val, Leu, Ile, Gly, Ser, or Thr; Xaa(2) is an Ile, Glu, Asp, Gly, Ala, Val, Leu, Ser, or Thr; Xaa(3) is a Gln, Glu, Asn, or Asp; Xaa(4) is an Ala, Thr, Gly, Val, Leu, Ile, or Ser; Xaa(5) is a Glu, Gly, Asp, Ala, Val, Leu, Ile, Ser, or Thr; Xaa(6) is a Tyr, Phe, or Trp; Xaa(7) is a Met, Thr, Ser, Gly, Ala, Val, Leu, or Ile; Xaa(8) is a Pro, Ser, Gly, Ala, Val, Leu, Ile, or Thr; Xaa(9) is an Asn, Ser, Gln, Gly, Ala, Val, Leu, Ile, or Thr; Xaa(10) is a Pro, Ser, Gly, Ala, Val, Leu, Ile, or Thr; Xaa(11) is an Arg, Lys, or His; Xaa(12) is a Pro, Ser, Gly, Ala, Val, Leu, Ile, or Thr.

In another embodiment, the sequences of heregulins and of neu differentiation factors (NDFs) can be included in the variant population, and used to generate a combinatorial ARIA library. In some instances, it may be desirable to include only the β-type EGF-like domains (e.g. derived from HRG-βs and NDF-βs), in that the $C_5$–$C_6$ sequences of the α-type EGF-like domains are much more divergent from ARIA. However, inclusion of the heregulins, NDFs, as well as Heparin-binding EGF-like growth factor (HB-EGF), amphiregulin (AREG), and Schwanoma-derived growth factor (SDGF), each shown in FIG. 3, produces a combinatorial library of the general formula (SEQ ID NO:47):

Cys-Xaa(1)-Xaa(2)-Xaa(3)-Xaa(4)-Xaa(5)-Xaa(6)-Xaa(7)-Cys-
Xaa(8)-Xaa(9)-Xaa(10)-Gly-Xaa(11)-Cys-Xaa(12)-Xaa(13)-

Xaa(14)-Xaa(15)-Xaa(16)-Xaa(17)-Xaa(18)-Xaa(19)-Xaa(20)-
Xaa(21)-Xaa(22)-Xaa(23)-Xaa(24)-Cys-Xaa(25)-Cys-Xaa(26)-
Xaa(27)-Xaa(28)-Xaa(29)-Xaa(30)-Gly-Xaa(31)-Arg-Cys or,

Cys-Xaa(1)-Xaa(2)-Xaa(3)-Xaa(4)-Xaa(5)-Xaa(6)-Xaa(7)-Cys-
Xaa(8)-Xaa(9)-Xaa(10)-Gly-Xaa(11)-Cys-Xaa(12)-Xaa(13)-
Xaa(14)-Xaa(15)-Xaa(16)-Xaa(17)-Xaa(18)-Xaa(19)-Xaa(20)-
Xaa(21)-Xaa(22)-Xaa(23)-Xaa(24)-Cys-Xaa(25)

wherein Xaa(1) is an Asp, Ala, Leu, or Asn; Xaa(2) is an Ile, Glu, Arg, or Ala; Xaa(3) is a Lys, or Glu; Xaa(4) is a Gln, Glu, Tyr, or Phe; Xaa(5) is a Lys, or Gln; Xaa(6) is an Ala, Thr, Asp, or Asn; Xaa(7) is a Phe; Xaa(8) is a Val, or Ile; Xaa(9) is an Asn, or His; Xaa(10) is a Gly, or an amino acid gap; Xaa(11) is a Glu, or Gly; Xaa(12) is a Tyr, Phe, Lys, or Arg; Xaa(13) is a Met, Thr, or Tyr; Xaa(14) is a Val, or Ile; Xaa(15) is a Lys, or Glu; Xaa(16) is an Asp, Glu, His, or Asn; Xaa(17) is a Leu; Xaa(18) is a Pro, Ser, Arg, or an amino acid gap; Xaa(19) is an Asn, Ser, Ala, or an amino acid gap; Xaa(20) is a Pro, or an amino acid gap; Xaa(21) is a Pro, Ser, or Glu; Xaa(22) is an Arg, Ala, Val, or an amino acid gap; Xaa(23) is a Tyr, Val, or an amino acid gap; Xaa(24) is a Leu, Thr, or an amino acid gap; Xaa(25) is an Arg, Lys, Ile, or His; Xaa(26) is a Pro, Ser, Gln, or His; Xaa(27) is an Asn, Pro, or Gln; Xaa(28) is a Glu, Gly, or Asp; Xaa(29) is a Phe, or Tyr; Xaa(30) is a Thr, His, or Phe; and Xaa(31) is an Asp, Ala, or Glu. In this contact, an amino acid gap is understood to mean the deletion of that amino acid position from the resulting peptide. For example, where above Xaa(8) is Val, Xaa(9) is Asn, and Xaa(10) is an amino acid gap. That portion of the EGF-like sequences would have the formula -Cys-Val-Asn-Gly-, rather than -Cys-Val-Asn-Gly-Gly where Xaa(10) is a glycine residue In similar fashion, the degeneracy provided by the inclusion of an EGF and TGF-α sequence can produce a combinatorial library of EGF-like domains having the general formula (SEQ ID NO:25):

Cys-Xaa(1)-Xaa(2)-Xaa(3)-Xaa(4)-Xaa(5)-Xaa(6)-Xaa(7)-Cys-
Xaa(8)-Xaa(9)-Xaa(10)-Gly-Xaa(11)-Cys-Xaa(12)-Xaa(13)-
Xaa(14)-Xaa(15)-Xaa(16)-Xaa(17)-Xaa(18)-Xaa(19)-Xaa(20)-
Xaa(21)-Xaa(22)-Xaa(23)-Xaa(24)-Cys-Xaa(25)-Cys-Xaa(26)-
Xaa(27)-Xaa(28)-Xaa(29)-Xaa(30)-Gly-Xaa(31)-Arg-Cys or,

Cys-Xaa(1)-Xaa(2)-Xaa(3)-Xaa(4)-Xaa(5)-Xaa(6)-Xaa(7)-Cys-
Xaa(8)-Xaa(9)-Xaa(10)-Gly-Xaa(11)-Cys-Xaa(12)-Xaa(13)-
Xaa(14)-Xaa(15)-Xaa(16)-Xaa(17)-Xaa(18)-Xaa(19)-Xaa(20)-
Xaa(21)-Xaa(22)-Xaa(23)-Xaa(24)-Cys-Xaa(25)

Wherein Xaa(1) is an Asp, Ala, Leu, Asn, or Pro; Xaa(2) is an Ile, Glu, Arg, Ala, Leu, or Asp; Xaa(3) is a Lys, Glu, or Ser; Xaa(4) is a Gln, Glu, Tyr, Phe, or His; Xaa(5) is a Lys, Gln, Asp, or Thr; Xaa(6) is an Ala, Thr, Asp, Asn, Gly, or Gln; Xaa(7) is a Phe, or Tyr; Xaa(8) is a Val, Ile, Leu, or Phe; Xaa(9) is an Asn, or His; Xaa(10) is a Gly, an amino acid gap, or Asp; Xaa(11) is a Glu, Gly, Val, or Thr; Xaa(12) is a Tyr, Phe, Lys, Arg, or Met; Xaa(13) is a Met, Thr, Tyr, or Phe; Xaa(14) is a Val, Ile, or Leu; Xaa(15) is a Lys, Glu, or Val; Xaa(16) is an Asp, Glu, His, Asn, Ala, or Gln; Xaa(17) is a Leu, or Glu; Xaa(18) is a Pro, Ser, Arg, or an amino acid gap; Xaa(19) is an Asn, Ser, Ala, or an amino acid gap; Xaa(20) is a Pro, or an amino acid gap; Xaa(21) is a Pro, Ser, Glu, or Asp; Xaa(22) is an Arg, Ala, Val, an amino acid gap, or Lys; Xaa(23) is a Tyr, Val, an amino acid gap, or Pro; Xaa(24) is a Leu, Thr, an amino acid gap, or Ala; Xaa(25) is an Arg, Lys, Ile, His, Asn, or Val; Xaa(26) is a Pro, Ser, Gln, His, or Val; Xaa(27) is an Asn, Pro, Gln, Val, or Ser; Xaa(28) is a Glu, Gly, or Asp; Xaa(29) is a Phe, or Tyr; Xaa(30) is a Thr, His, Phe, Ile, or Val; and Xaa(31) is an Asp, Ala, or Glu. However, it is noted that as the ability of EGF and TGF-α to induce ARIA-like responses in a cell has been tested and found to be negligible, such a combinatorial library is likely to have a significant population of ARIA antagonists as well as peptides unable to bind an ARIA receptor. The former being separable from the later by its ability to bind such a receptor in a panning assay, such as described below.

In another embodiment, a degenerate sequence library can be created to be entirely random, within the general restrictions of EGF-like sequences, between C1 and C2 as well as C5 and C6, as these sequence are the most varied between the chicken and rat clones of ARIA as well as the heregulins and NDF. Such a library can be represented by the general formula (SEQ ID NO:23)

Cys-Z-Cys-Val-Asn-Gly-Gly-Xaa(1)-Cys-Xaa(2)-Xaa(3)-Val-Lys-Asp-Lys-Xaa(4)-Xaa(5)-Pro-Xaa(6)-Arg-Tyr-Leu-Cys-Xaa(7)-Cys-Y-Cys wherein Xaa(1) is a Glu, or Gly; Xaa(2) is a Tyr, or Phe; Xaa(3) is a Met, or Thr; Xaa(4) is a Pro, or Ser; Xaa(5) is an Asn, or Ser; Xaa(6) is a Pro, or Ser; Xaa(7) is an Arg, or Lys; Xaa(8) is a Pro, or Ser; Z represents 4 to 14 amino acids which can be the same or different; and $X_5$ represents 8 to 14 amino acids which can be the same or different.

In yet another embodiment, all possible EGF-like sequences can be substituted into ARIA in place of those naturally occurring, and the recombinant molecules tested for activity. In such an embodiment, the EGF-like domain of ARIA is given by the general formula, as set out above, $CX_1CX_2CX_3CX_4CX_5C$, where C is a cysteine, $X_1$ represents 4 to 14 amino acids which can be the same or different, $X_2$ represents 3 to 8 amino acids which can be the same or different, $X_3$ represents 4 to 14 amino acids which can be the same or different, $X_4$ is any amino acid, and $X_5$ represents 8 to 14 amino acids which can be the same or different.

In similar fashion, larger portions of the ARIA homologs can be aligned and used to create combinatorial libraries of potential ARIA homologs. In an illustrative embodiment, combinatorial libraries can be generated to include sequences from the Ig-like domain through the EGF-like domain.

There are many ways by which the library of potential ARIA homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential ARIA sequences. The synthesis of degenerate oligonucleotides is well known in the art (see for example Narang, SA (1983) *Tetrahedron* 39:3; Itakura et al. (1981) *Recombinant DNA, Proc 3rd Cleveland Sympos. Macromolecules,* ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477), and such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815.

A wide range of techniques are known in the art for screening gene products of combinatorial libraries made by point mutations, and for screening cDNA libraries for gene products having a certain property. Such techniques will be generally applicable to rapid screening of the gene libraries generated by the combinatorial mutagenesis of ARIA and related proteins. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate ARIA sequences created by combinatorial mutagenesis techniques.

In one embodiment, the combinatorial library is designed to be secreted (e.g. the polypeptides of the library all include a signal sequence but no transmembrane or cytoplasmic domains), and is used transfect a eukaryotic cell that can be co-cultured with muscle cells. Functional ARIA secreted by the cells expressing the combinatorial library will diffuse to neighboring muscle cells and induce formation of AChR. Using antibodies directed to AChR epitopes, the pattern of detection of AChR induction will resemble a gradient function, and will allow the isolation (generally after several repetitive rounds of selection) of cells producing active ARIA homologs. Likewise, ARIA antagonists can be selected in similar fashion by the ability of the cell producing a functional antagonist to protect neighboring cells from the effect of ARIA added to the culture media.

To illustrate, target cells (e.g. rat L6 muscle cells) are cultured in 24-well microtitre plates. CHO cells are transfected with the combinatorial ARIA gene library (for instance, cloned into the plasmid pcDNAI/amp as described below) and cultured in a cell culture insert (e.g. Collaborative Biomedical Products, Catalog #40446) that are able to fit into the wells of the microtitre plate. The cell culture inserts are placed in the wells such that recombinant ARIA homologs secreted by the cells in the insert can diffuse through the porous bottom of the insert and contact the target cells in the microtitre plate wells. After a period of time sufficient for functional forms of ARIA to produce a measurable response in the target cells, the inserts are removed and the effect of ARIA on the target cells determined. For example, where the target cell is a muscle cell and the activity desired from the ARIA homolog is the induction of AChR, then fluorescently-labeled BgTx can be used to score for AChR induction in the target cells as indicative of a functional ARIA in that well. Cells from the inserts corresponding to wells which score positive for activity can be split and re-cultured on several inserts, the process being repeated until the active clones are identified.

In yet another screening assay, the candidate ARIA gene products are displayed on the surface of a cell or viral particle, and the ability of particular cells or viral particles to bind an ARIA-binding protein (such as an ARIA receptor, e.g. the putative receptor $p185^{HERB4}$) via this gene product is detected in a "panning assay". For example, expression vectors encoding a candidate ARIA sequence that includes a can be used to transfect cells which ordinarily do not bind significantly to a particular ARIA-binding protein (such as an ARIA receptor). For instance, the gene library can be cloned into the gene for a surface membrane protein of a bacterial cell, and the resulting fusion protein detected on the surface of the bacteria (Ladher et al., WO 88/06630; Fuchs et al. (1991) Bio/Technology 9:1370–1371; and Goward et al. (1992) TIBS 18:136–140). In another embodiment, the transmembrane domain of ARIA can be included in the candidate ARIA gene such that the combinatorial library is membrane bound. Ligand-affinity or panning methods for assessing expression of membrane-bound proteins are also well established (Aruffo et al. (1987) PNAS 84: 8573; Seed et al. (1987) PNAS 84:3365; and Kiefer et al. (1990) PNAS 87:6985). Such panning assays can be carried out using any insolubilized substrate which would act to sequester cells displaying an ARIA homolog, such as, to illustrate, an extracellular portion of $p185^{HERB4}$. In a similar fashion, fluorescently labeled molecules which bind ARIA can be used to score for potentially functional ARIA homologs. Cells can be visually inspected and separated under a fluorescence microscope, or, where the morphology of the cell permits, separated by a fluorescence-activated cell sorter.

In yet another embodiment, the gene library is expressed as a fusion protein on the surface of a vital particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage encodes the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the vital particle (Ladher et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461).

To illustrate, the recombinant phage antibody system (RPAS, Pharamacia Catalog number 27-9400-01) can be easily modified for use in expressing and screening the present ARIA combinatorial libraries. For instance, the pCANTAB 5 phagemid of the RPAS kit contains the gene which encodes the phage gIII coat protein. The ARIA combinatorial gene library is cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate ARIA gene insert. The resulting recombinant phage contain phagemid DNA encoding a specific candidate ARIA, and display one or more copies of the corresponding fusion coat protein. The phage-displayed candidate ARIAs which are capable of binding an ARIA receptor are selected or enriched by panning. For instance, the phage library can be applied to cultured skeletal muscle cells (e.g. rat L6 cells, ATCC CRL 1458) at 4° C. (to prevent endocytosis), and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for ARIA homologs which can then be screened for further biological activities in order to differentiate agonists and antagonists.

We have also discovered that the mechanism of action of ARIA appears to be strongly correlated to the tyrosine phosphorylation of a 185 kD (p185) protein present in cells sensitive to ARIA treatment. Western blots of chick, rat, postnatal mouse and human muscle lysates, derived from cells treated with ARIA and developed with an anti-phosphotyrosine antibody, have demonstrated that ARIA induces phosphorylation of p185. Significantly, no ARIA-induced phosphorylation of p185 was observed in cultures of chick fibroblasts that did not contain muscle cells. The treatment of ciliary ganglion neurons with ARIA similarly results in the phosphorylation of p185.

EGF, PDGF and insulin all promote tyrosine phosphorylation of chick muscle protein, but the phosphorylated protein could be easily distinguished from p185. FGF, CSF1 and NGF had no effect at all. None of these factors induced phosphorylation of the same band as ARIA. Moreover, none of the factors increased the synthesis of AChRs in the surface membrane of the cells. Agrin, a protein which has previously been shown to promote the aggregation, but not the synthesis of, AChRs likewise failed to affect the phosphorylation of p185.

ARIA-induced phosphorylation was rapid and transient, a clearly antibody-stained band being visible within 1 minute of treatment of the cells with ARIA. At each stage of chromatographic purification, the phosphorylation of p185 was highly correlated with ARIA fractions scoring positive for ARIA by the receptor-insertion bioassay. In addition to the correlation between fractions which scored positive by receptor bioassays and p185 phosphorylation, both activities exhibited nearly identical dose response curves. Suramin, a drug known to interfere in the binding of many growth factors to their receptors, blocked both the creation of new $\alpha$-BTX binding sites as well as p185 phosphorylation with the same dose dependence. Importantly, suramin has no effect on tetradotoxin (TTX) induced AChR synthesis over the same dose range.

ARIA appears to bind to an extracellular domain of p185, as evidenced by the apparent cross-linking of the two proteins to form $\cong$400 kD (p185 dimer plus ARIA) and $\cong$220 kD species (p185 plus ARIA).

It is most likely that p185 is a tyrosine kinase, and that binding of ARIA to p185, and the ultimate phosphorylation of p185, is one of the first steps in an ARIA-induced cascade that ultimately regulates ion channel levels, such as by mechanisms similar to the observed regulation of nicotinic AChR subunit expression.

In order to determine if the p185 signal could be accounted for as phosphorylation of the neu proto-oncogene protein (Yarden et al. 1988 *Annu. Rev. Biochem.* 57:443), the ability of all of the ARIA-induced phosphotyrosine band to be precipitated by anti-neu antibodies was tested, as was the ability of anti-Ptyr antibodies to precipitate neu in ARIA treated cells. Two monoclonal antibodies (Oncogene Science Inc., Catalog Nos. OP15 (Ab3) and OP16L(Ab4)) capable of immunoprecipitating the rat neu protein were used for these experiments: Ab3, an IgG directed against the intracellular domain of neu; and Ab4, an IgG directed against the extracellular domain.

L6 cells were treated with chick brain purified ARIA for 1 hour. Treated and control cells were lysed in Tris buffer solution (pH5) containing 1% NP-40, 150 mM NaCl, 1 mM ortho-vanadate and protease inhibitors. Insoluble components were separated by centrifugation and the supernatant was incubated with either 1) anti-Ptyr conjugated to agarose beads, 2) Ab3 and protein-G agarose beads, or 3) Ab4 and protein-A agarose beads.

Experimental results suggest that immunoprecipitation of p185 with the anti-Ptyr antibody is quantitative, while immunoprecipitation of the neu protein by either anti-neu antibody is not. Therefore, and in order to obtain quantitative removal of the neu protein from the supernatant, three consecutive incubations (3 hours each) with fresh batches of antibodies were performed. Thereafter, each batch of beads and the supernatant were tested for the presence of p185 and the neu protein by western blot.

Anti-Ptyr did not precipitate any detectable amount of neu from control cells, while some neu signal was detected in the precipites of treated cells. However, most of the neu signal remained in the supernatant, while all the phosphorylated p185 signal was removed by the beads.

Using the anti-neu antibodies we were able to remove quantitatively the neu protein from the supernatant. Interestingly in both cases we did not remove the p185 signal completely. In the case of Ab4 some p185 signal was precipitated by the first round of beads, a much smaller amount with the second and none with the third. The amount of precipitated p185 signal nevertheless was much less than the signal left in the final supernatant. Ab3 very effectively precipitated neu, without bringing down any p185 signal and, in treated cells, substantially all the tyrosine phosphorylated signal remained in the supernatant.

EXAMPLE ONE

AChR Bioassay

Mononucleated cells were dissociated from pectoral muscles of 10–12 day-old chick embryos (E10) as previously described (Buc-Caron et al., 1983 *Dev. Biol.* 95:378). To reduce the number of fibroblasts, the cells were suspended in complete medium and plated in uncoated 100-mm tissue culture dishes (Falcon Labware, Oxanard, Calif.) for 30 min at 37° C. Unattached cells were collected and plated in gelatin-coated, 96-well Micro Test culture plates (Falcon Labware) at a density of 50,000/well in 100 µl of Eagle's minimal essential medium supplemented with horse serum (10% vol/vol), glutamine (1 mM), penicillin (50 U/ml), streptomycin (50 µg/ml), and ovotransferrin (40 µg/ml). The cells were fed with 100 µl of medium on days 3 and 5. On day 7 they were fed with 60 µl of medium or 50 µl of medium plus 10 µl of a test fraction, and the number of AChRs was measured 24 h later (see below). Aliquots of column fractions to be assayed were dried in a Speed-Vac centrifuge (Savant Instruments, Inc., Hicksville, N.Y.) and redissolved in complete medium. Samples that contained nonvolatile material were first desalted on Sep-Pak $C_{18}$ cartridges (Waters Associates Millipore Corp., Milford, Mass.). Samples containing <1 µg of protein were supplemented with 10 µg BSA.

To measure the number of surface AChRs the cells were incubated in complete medium containing 5 nM [$^{125}$I]$\alpha$-BTX for 1 h at 37° C. The cells were washed twice by immersing the plates in 1 liter $Ca^{++}$-free Hank's balanced salt solution (BSS) containing 2% BSA and then solubilized in 150 µl of 1 N NaOH containing sodium deoxycholate (0.5 mg/ml). The amount of [$^{125}$I]$\alpha$-BTX bound was determined with a gamma counter Nonspecific binding, taken as the amount of [$^{125}$I]$\alpha$-BTX bound in the presence of $10^{-7}$ M unlabeled $\alpha$-BTX, was subtracted in each case.

The rate of incorporation of AChRs into the surface membrane was determined as described by Devreotes and Farobrough (1975) *J. Cell Biol* 65:335, incorporated by reference herein. All receptors exposed on the muscle surface were blocked with unlabeled $\alpha$-BTX ($10^{-7}$ M for 1 h at 37° C.). The cells were washed thoroughly, returned to the incubator in 100 µl of fresh medium, and the number of new toxin binding sites was assayed with [$^{125}$I]$\alpha$-BTX at various intervals thereafter.

α-BTX was iodinated by the chloramine-T-catalyzed reaction (Hunter and Greenwood, 1962 Nature 19:495), and monoiodinated derivatives were purified by size exclusion (Sephadex G-10; Pharmacia Fine Chemicals, Inc., Piscataway, N.J.) and cation exchange (CM-Sephadex; Pharmacia Fine Chemicals) chromatography. The specific activity of monoiodinated toxin, estimated by competition with known concentrations of unlabeled α-BTX, ranged between 800 and 1200 cpm/fmol in different preparations.

EXAMPLE TWO

Purification of ARIA

Purification of ARIA was carried out by reverse-phase, ion exchange, and size exclusion chromatography in the following steps. (1) 3000 frozen adult chicken brains were crushed in dry ice and delipidated by grinding in acetone at −20° C. The slurry was collected on Whatman No. 54 paper (Whatman Chemical Separation Inc., Clifton, N.J.), washed with diethylether (−20° C.), and stored at −90° C. Subsequent steps in the extraction were performed at 4° C. (2) The residual brain "mud" was acid extracted with a cocktail of 2% trifluoroacetic acid (TFA), 5% formic acid, 1N hydrochloric acid, 0.1M sodium chloride, 0.01% thiodiglycol, 1 ug/mL each of pepstatin, leupeptin, and phenylmethylsulphonyl fluoride, and 10 mM EDTA. After centrifugation at 6000 rpm for 60 minutes in a GSA rotor (Sorvail Instruments), the supernatant was filtered through Whatman No. 54 paper. (3) The filtered extract was then batch absorbed on a C18 resin that had been preequilibrated with 0.1% TFA. The resin was washed with 0.1% TFA, and material bound to the resin was eluted with isopropyl alcohol. (4) The extract was brought to pH 7.0 with 0.1N NaOH, and centrifuged to remove any precipitate. The neutralized extract was chromatographed on a CM sepharose column equilibrated in 25 mM 4-morpholineethanesulfonic acid (MES) (pH6) and eluted with a gradient of sodium chloride (NaCl). (5) Eluate fractions containing ARIA were brought to pH 3.0 with TFA and chromatographed on a Vydac C4 reverse-phase column equilibrated with 0.1% TFA and eluted with a gradient of isopropyl alcohol. (6) ARIA containing fractions were pooled and chromatographed on a heparin-TSK column equilibrated with phosphate-buffer saline (PBS) and eluted with a gradient of NaCl. Each fraction was analyzed for ARIA by receptor insertion assays (see Example one) as well as for the presence of Ch-PrLP by western blot analysis using anti-PrLP antibodies. Fractions scoring positive for ARIA but not Ch-PrLP were pooled. (7) The pooled fractions were chromatographed on a Superdex 75 16/120 gel filtration column (FPLC) equilibrated and run with PBS. (8) The pooled ARIA containing fractions of the Superdex column were chromatographed on a C4 reverse-phased column equilibrated in 0.13 % heptafluorobutyric acid and eluted with a gradient isopropyl alcohol. (9) The ARIA containing C4 fractions were then pooled and chromatographed on a microbore Vydac C18 reverse-phase column equilibrated in 0.1 percent TFA and eluted with a step gradient of acetonitrile in TFA.

EXAMPLE THREE

PCR primers from Tryptic Fragments

Bioactive eluate fractions of the C18 reverse-phase chromatograph of Example two were assayed for ARIA by the receptor bioassay as well as analyzed by SDS-PAGE visualized by silver staining in order to exclude contaminants. Appropriate fractions were pooled and partially digested with trypsin, the resulting peptides separated by reverse-phase chromatography. The chromatographed fragments were then analyzed by Edman degradation, and two of the chromatographic fractions yielded single sequences. The chemically determined amino acid sequence for each of those tryptic fragments is as follows:

Peptide 1: Asn-Arg-Pro-Glu-Asn-Val-Lys (SEQ. ID NO. 5)

Peptide 2: Ala-Thr-Leu-Ala-Asp-Ala-Gly-Glu-Tyr-Ala-Cys-Arg (SEQ. ID NO. 6)

From these amino acid sequences, homology to rat NDF (Yarden et al.) and the human heregulins (Holmes et al.) was noted. The sequence homology with these proteins suggested that Peptide 1 was the more N-terminal peptide fragment of the two. To construct PCR primers, the sense oligonucleotide primer was based on the amino acid sequence of Peptide 1 and the antisense oligonucleotide primer was based on the amino acid sequence of Peptide 2. A set of degenerate oligonucleotide primers for PCR were designed having the following nucleotide sequences.

Primer 2S: GICCIGARAAYGTNAAG (SEQ. ID NO. 7)
Primer 2A: CKRCAIGCRTAYTCNCC (SEQ. ID NO. 8)

Wherein primer 2S corresponds to the sense codons of peptide 1, and primer 2A corresponds to the antisense codons of peptide 2.

EXAMPLE FOUR

PCR Amplification of ARIA sequences in Spinal Cord RNA

Chick spinal cord RNA was prepared from the spinal cords of embryonic day 19–20 chicks by the guanidinium thiocyanate/phenol extraction procedure of Chomczynski (Chomczynski U.S. Pat. No. 4,843,155; Chomczynski et al. 1987 Anal Biochem. 162:156, incorporated by reference herein). Polyadenylated RNA was reverse transcribed using an oligo(dT)$_{12-18}$ primer and Moloney Murine Leukemia Virus (M-MLV) reverse transcriptase (see for example Molecular Cloning, A Laboratory Manual, Sambrook, Fritsch and Maniatis Eds 1989: Cold Spring Harbor Laboratory Press; Chapter 5, incorporated by reference herein). Basically, 2 µg of total RNA was annealed to 1 µg of oligo(dT)$_{12-18}$ in a 20 µL volume of buffer for 30 minutes. The annealing mixture was diluted with reverse transcriptase buffer, dithiothreitol (DTT, 10 mM final), and dNTPs (400 µM) to a final volume of 50 uL. 200 U of M-MLV reverse transcriptase (GibCo-BRL, Gaithersburg Md., Catalog No. 8025) were added and the reaction was incubated for 60 minutes at 42° C., then heat inactivated for 15 minutes at 65° C.

Using the primers 2S and 2A, PCR was performed on the chick spinal cDNA (see the Mullis U.S. Pat. No. 4,683,202, the Norman et al. U.S. Pat. No. 4,800,159, and the Erlich et al. U.S. Pat. No. 4,965,188, incorporated by reference herein). Briefly, PCR was performed in a 100 uL reaction containing 5 uL of the reverse transcription mixture, 400 µM dNTPs, 1 µg of each primer, 1X Taq DNA polymerase buffer, and 5 U of Taq DNA polymerase (Boehringer-Mannheim, Indianapolis, Ind., Catalog No. 1146-165). The PCR was carried through 40 cycles of 94° C. for 1 minute, 44° C. for 1 minute, and 72° C. for 1 minute.

The PCR products were run out on an agarose gel and selected bands cut out and purified. From the noted homology with rat NDF, it was predicted that a 94 nucleotide fragment should be amplified by these two primers. From the agarose gel, a 97 nucleotide cDNA from the reverse transcribed chick spinal cord RNA was isolated. The purified products were ligated into the PCR-II vector using the TA Cloning™ Kit (Invitrogen Corp, San Diego Calif., Catalog No. K2000) (Clark 1988 *Nucleic Acids Res.* 16:9677; Grahm et al. 1991 *PNAS* 88:10267; and Jarolim et al. 1991 *PNAS* 88:11022, incorporated by reference herein). The cloned inserts were sequenced by dideoxy chain termination (Sanger et al. 1977 *PNAS* 74:5463, incorporated by reference herein). The sequence of the 97 nucleotide long cDNA was determined to be:

97b fragment:

```
GG  CCG GGA AAT GTC AAG ATC CCC AAA AAG CAA AAG AAA
TAC TCT GAG CTT CAT ATT TAT AGA GCC ACG TTG GCT GAC
GCT GGG GAA TAC GCC TGC CG (SEQ. ID NO. 9)
```

EXAMPLE FIVE

Screening a λgt10 Chicken Brain cDNA Library

The 97-mer fragment was labeled with $^{32}P$ using the random oligonucleotide priming method (see Feinberg et al. 1983 *Anal. Biochem.* 132:6; and Feinberg et al. 1984 *Anal. Biochem.* 137:266, incorporated by reference herein), [α-$^{32}P$]-labeled dCTP and the Primit™ labeling kit (Stratagene, LaJolla, Calif.), such that labeled probes were generated ranging in size from 10 to 97 nucleotides. These $^{32}$p-labeled probes were then used to screen a Ranscht E13 chicken brain cDNA λgt10 library (See Ranscht et al. 1988, *J. Cell Biol.* 107:1561, incorporated by reference herein).

Briefly, the recombinant phage and plating bacteria were mixed and incubated at 30° C., added to top agarose (2xYT/Mg/Maltose) and the mixture transferred to 2xYT plates. The plates were incubated at 37° C. until there were visible but not confluent plaques, and then incubated at 4° C.

Duplicate lifts were made of each cold plate using nitrocellulose filters. The filters were denatured and then baked at 70° C., in vacuo, for 2 hours (see Benton et al. 1977 *Science* 196:180, incorporated by reference herein).

The baked filters were prewashed in 1000 µL of 50 mM Tris-HCl (PHS), 1M NaCl, 1 mM EDTA, and 0.1% SDS at 37° C. for about 1 hour. The filters were then pre-hybridized in 40% formamide/6X SSC/0.2% SDS with 100 µg/ml salmon sperm DNA at 37° for about 5.75 hours. The pre-hybridized filters were than hybridized in 40% formamide/6X SSC/0.2% SDS with $^{32}$P-labeled probe (see above) and 100 µg/ml salmon sperm DNA at 37° C. overnight, and washed to a final stringency (high) of 0.1X SSC/0.1% SDS at 45° C.

The filters were then exposed to x-ray film at –70° C. and autoradiograms developed. Alignment of the autoradiogram with the original plates from which the nitrocellulose lifts were made allowed scoring for positive hybridization by comparison of silver grain density with the λgt10 plaques. Phage which scored positive for hybridization with the radiolabeled probes were isolated from the agarose plates and rescreened by the above method.

Phage isolated after the second round were subjected to PCR amplification using primers directed to λgt10 sequences across the EcoRI site in the cI gene. The longest cDNA clone isolated was 2.4 kb insert comprising the sequence shown in FIG. 1.

EXAMPLE SIX

Expression of recombinant ARIA

The 2.4 kb cDNA representing the largest chicken ARIA clone was cloned into the unique EcoRI site of the eukaryotic expression vector pcDNAI/Amp (Invitrogen Corp.; San Diego, Calif.; catalog #V460-20) which contains an SV40 virus origin of replication to allow high level of expression in COS cells. The insert is under the control of the enhancer/promoter region of the immediate early gene of cytomegalovirus. Constructs were prepared harboring the 2.4 kb cDNA in both the appropriate and the reverse orientation. The different plasmid constructs were prepared after growth in bacteria to produce large enough amounts for transfection experiments.

Plasmid constructs were transfected into monkey COS-7 cells using the DOTAP Transfection Reagent (Boehringer-Mannheim; Indianapolis, IN; Catalog #1202-375). Briefly 1.7 µg of a specific plasmid was mixed with 10 µg of DOTAP and allowed to stand for 10 minutes at room temperature. The mixture was then applied to 35 mm dishes of COS-7 cells growing in DMEM with 10% FBS. The transfection mixture was left on the cells for 18 hours. After this incubation the transfection mixture was removed and the medium replaced with fresh MEM/10% Horse serum/2% Chick embryo extract. The cells were allowed to grow for 48 hours to condition their medium with secreted factors. The conditioned medium was collected and used either undiluted or at several dilutions in an AChR incorporation rate assay with primary chicken muscle cultures or in phosphorylation assays of p185 on rat L6 cells.

EXAMPLE SEVEN

Cloning and Expression of Rat ARIA

Total RNA was isolated from postnatal day 20 (P20) rat spinal cord by the method of Chomcyznski. 2 µg of RNA was annealed to 1 µg of oligo(dT)$_{12-18}$ by heating to 65° C. for 10 minutes followed by placing the sample on ice for 5 minutes. Reverse transcription buffer, dNTPs (400 µM final), DTT (10 mM final), RNAse inhibitor, and 400 U of Moloney Murine Leukemia virus Reverse Transcriptase (Gibco-BRL; Gaithersburg, Md.) were added in a final reaction volume of 50 µl. The samples were incubated for 1 hour at 42° C. followed by 15 minutes at 65° in order to inactivate the enzyme.

Rat spinal cord derived cDNA was subjected to polymerase chain reaction using two combinations of primers corresponding to sequences that border the described EGF-like domain of rat NDF (Wen et al. 1992 *Cell* 69:559). The outermost pair of oligonucleotides correspond to the following sequences: GCGCAAACACTTCTTCATCCAC (SEQ. ID NO. 10) (this represents most of the sense coding information for amino acids 162–169, GANTSSST, (SEQ. ID NO. 11), of the rat NDF sequence) and CACCACACA-CATGATGCCGAC (SEQ. ID NO. 12) (this represents most of the antisense strand corresponding to amino acids 256–262, VGIMCVV, (SEQ. ID NO. 13)). The innermost pair of the oligonucleotides were designed to allow for amplification from the PCR products made using the outer pair of oligonucleotides but they also contained mutations relative to the sequence for rat NDF that would allow for the orientation specific cloning of the PCR product, after restriction enzyme digestion, directly into the bacterial fusion protein expression vector pMAL-p2 (N.E. Biolabs;Beverly, Mass.; catalog #800). The sequence of the inner oligonucleotides was as follows: CACGACTAGTACTAGCCATCTC (SEQ. ID NO. 14), corresponding to the sense coding information for amino acids 172–179 of rat NDF with mutations that were introduced to create a restriction site for the enzyme ScaI that would cleave exactly between codons and leave the reading frame intact; and CGACAAGCT-TCTAGTAGAGTTCC (SEQ. ID NO. 15), corresponding to the antisense strand of the coding information for amino acids 236–244 of rat NDF with mutations relative to the original sequence that would create an in-frame stop translation codon as well as a site for the restriction enzyme HindIII that would allow for cloning into the pMAL-p2 vector. Using these combinations of primers, PCR reactions were set up as follows: 2 μl of spinal cord cDNA reverse transcription reaction, 1 μg of each primer, 400 μM dNTPs, Taq DNA Polymerase Reaction buffer and 2.5 U TAQ DNA Polymerase (Boehringer-Mannheim; Indianapolis, Ind. Catalog #1146–165). The reactions were cycled as follows: 94° C. for 10 minutes, 52° C. for 2 minutes, 72° C. for 2 minutes, followed by 39 cycles of 94° for 1.5 minutes, 52° C. for 1.5 minutes, 72° C. for 2 minutes, followed by a final cycle of 94° C. for 2 minutes, 52° C. for 2 minutes and 72° C. for 10 minutes. Products were analyzed by agarose gel electrophoresis.

The expectation based upon the sequence of rat NDF was for a PCR product of 302 bp for the outer primer pair and a PCR product of 215 bp for the inner primer pair. The agarose gel analysis revealed products of 317 and 230 bp respectively for the outer and inner primer pairs. The PCR products were cloned using the vector pCR-II and the TA cloning kit (Invitrogen Corp.;San Diego, Calif.; catalog #K2000-01). Sequence analysis of these clones indicated that both identified an EGF-like domain corresponding closely to the ARIA identified in chicken, and the human heregulin B-1 sequence. The inner pair of primers contained mutations which allowed for the directed cloning of the cDNA fragment into pMAL-p2. This vector contains the gene for the maltose binding protein (MBP) of $E.$ $coli$ connected to a unique group of cloning sites that allow for expression of new sequences as fusion proteins with MBP and their subsequent purification by affinity chromatography on maltose resin. The cloning site also bears a recognition sequence for the factor Xa protease just prior to the site of insertion of foreign cDNAs. The construct also bears an inducible promoter for the fusion allowing for the induction of expression of the fusion protein by adding isopropyl-β-D-thiogalactopyranoside (IPTG) to the culture.

In the vector pMAL-p2, the MBP gene includes information encoding a signal sequence which targets MPB fusion proteins to the periplasmic space. Periplasmic proteins may have appropriate disulfide bond formation and can be purified by less harsh methods than are required for fusion proteins sequestered intracellularly.

A portion of the PCR product described above, which includes the EGF-like domain, was prepared by digestion with ScaI and Hind3 and cloned into pMAL-p2 prepared by digestion with XmnI and Hind3. This plasmid was transformed into DH5-α bacteria. Sequencing confirmed that the plasmid encoded the expected sequence fused in frame to the maltose binding protein.

For production of the fusion protein, cultures were grown to a density of $A_{600}$=0.5, then induced by the addition of IPTG to a final concentration of 0.3 mM. The cultures were incubated for an additional 2 hours, then the bacteria were harvested by centrifugation. The pellet was resuspended in a buffer consisting of 30 mM tris HCl (pH 8.0), 20% sucrose, 1 mM EDTA and incubated to this buffer for 5–10 min. The bacteria were again pelleted, resuspended in ice cold 5 mM $MgSO_4$ and stirred in this solution in an ice water bath for 10 min. The bacteria were again pelleted by centrifugation and the solution was decanted off. This solution is the "Cold Osmotic Shock Fluid" containing the released fusion protein. Presence of the fusion protein was confirmed by SDS polyacrylamide gel analysis.

Treatment of L6 cells and chick myotubes with the cold osmotic shock fluid containing rat ARIA fusion protein produces striking phosphorylation of p185 in rat L6 and chick myotubes.

In the set of experiments described above, PCR was performed using the primer corresponding to the sequence of nucleotides surrounding the EGF-like domain of rat NDF. As described, in the creation of the EGF-like domain/pMAL fusion vector, the PCR products generated defined the presence of a protein in rat spinal cord harboring a β-1 form of an EGF-like motif.

In the next set of PCR experiments, primers were chosen in order to amplify the sequence of an NDF related cDNA between the beginning of the EGF-like domain and the translation stop codon as well as the end of the EGF-like domain and the translational initiator methionine region. The oligonucleotide CATTTTACCTTTCGCTATGAGGAG (SEQ. ID NO. 16) ("3-AI"), which is the antisense strand corresponding to nucleotides 1586–1609 of the rat NDF sequence of Wen et al., was paired in PCR amplification with the oligonucleotide GCGCAAACACTTCTTCATCCAC (SEQ. ID NO. 17) ("4-SO"), which corresponds to nucleotides 821–842 of the rat NDF sequence. Using P20 rat spinal cord derived cDNA as a template for PCR, this amplification should have produced a band of 788 bp. The product visualized in this reaction was consistent with this size range but could not be defined within an error of less than approximately +/–20 bp.

Further PCR was performed with a pair of primers that would allow for amplification between the membrane spanning domain of NDF and its N-terminal methionine region. The oligonucleotides corresponded to the following sequences: CACCACACACATGATGCCGAC (SEQ. ID NO. 12) ("4-AO") representing the antisense strand of the sequence of rat NDF between nucleotides 1107–1122. The second oligonucleotide used in this PCR contained the sequence CTCATCTTCGGCGAGATGTCTG (SEQ. ID NO. 18) ("3-S1"), corresponding to nucleotides 322–343 of the rat NDF sequence, the region containing the initiator methionine (underlined in sequence). PCR with these oligonucleotides should have produced an 800 bp product. However, we were unable to amplify any product indicating that the N-terminal sequence of the published NDF sequence was not likely present in the spinal cord form. It is known from the PCR described in the fusion-protein section that the sequence represented by the oligonucleotide corresponding to nucleotides 1107–1122 (within the transmembrane domain sequence) was present.

Owing to the novel sequences found within the chicken ARIA cDNA, we performed PCR from P20 rat spinal cord cDNA using oligonucleotides that would include the spacer region sequence that is located between the Immunoglobulin (Ig) like domain and the EGF-like domain, the corresponding region of the chicken bearing the described Nex-2, one of the novel sequences. Oligonucleotides were designed based on the rat NDF sequences, and represented the sequence corresponding to: 1) the sense strand of nucleotides 670–692, TGCAAAGTGATCAGCAAGTTAGG (SEQ. ID NO. 19) ("7S"), which codes for amino acids 112–118 of the rat NDF sequence and 2) the antisense strand of nucleotides 1107–1122 of the rat NDF sequence ("4-AO", see above). Compared to the sequence of the published rat NDF cDNA, we expected to obtain a PCR product of 453 however, two prominent PCR products in the range of 350–475 bp were seen (the accuracy of estimation being +/−10bp) after agarose gel analysis.

Additional PCR amplifications were performed using the oligonucleotide corresponding to the antisense sequence of nucleotides 1107–1122 ("4-AO" above) in combination with a sense strand oligonucleotide corresponding to nucleotides 447–469 of the published rat NDF sequence, CAGATTGAAAGAAATGAAGAGCC (SEQ. ID NO. 21) ("6S"). After the results of the previous PCR amplifications we would have anticipated products of 691 bp and 589 bp representing both B1 forms (i.e., one corresponding to NDF and the other to ARIA) with either of the different spacer region exons being represented as described above. After analyzing the amplified products on an agarose gel, we identified (+/−15 bp) a number of bands measuring between 600 and 700bp.

Sequence analysis of the PCR products amplified from the rat spinal cord library revealed that a number of different variants of ARIA exist. Partial amino acid sequences (determined from the nucleotide sequence) for a number of illustrative rat ARIA clones are provided in the sequence listing, namely SEQ ID NOS. 4 and 32–36. As the 5' end of the coding region of each of the rat ARIA clones was not sequencable using primers directed to heregulin/NDF 5' sequences, is believed that this sequence, Nex-1, is unique with respect to the heregulins and NDF.

The Nex-2 exon sequence determined for the rat ARIA clones is shown here to be heterogenous in size. The partial sequencing of the B1-1 clone (SEQ ID NOS. 3 and 4) reveals a Nex-2 sequence that shares considerable homology with the corresponding spacer region between the EGF-like and Ig-like domains of the heregulins. However, other ARIA clones isolated from the rat spinal cord library possess Nex-2 sequences which, while sharing some homology with the heregulins, are truncated so as to be close in size to the Nex-2 sequence identified in chicken ARIA. For instance, Nex-2 can be ASANTTTVESNA (SEQ ID NOS. 32, 33, and 35), or TSSS (SEQ ID NO. 36). Interestingly, each of these Nex-2 sequences, when compared to the B1-1 clone and the heregulins, lack at least one of the potential N-linked glycosylation signals present in the spacer sequences. Such a feature, which may arise, for example, by differential splicing, may serve to alter the interaction of ARIA with extracellular matrix components. In a similar fashion, the 5' end of the heregulins contain a potential glycosaminoglycan attachment sequence, as well as a potential nuclear localization signal, which are not present in at least the sequenced chicken ARIA clones, and therefore possibly absent from the rat ARIA.

All of the PCR reactions described herein were performed under the same cycling conditions as were described for the section regarding the preparation of the EGF-like domain for cloning into the pMAL-p2 fusion expression vector. PCR reactions were performed using 5 µl of reverse transcription reaction for P20 rat spinal cord cDNA. They all used 1 µg of the appropriate primers.

EXAMPLE EIGHT

Further Isolation of chicken ARIA clones

In similar fashion to the methodology described above in both Examples Five and Seven, partial sequences for a number of other chicken ARIA cDNA clones were obtained using primers designed from the cDNA clone shown in FIGS. 1A–1D (SEQ ID NO. 1). Using primers to the nucleotides encoding the N-terminal end of the EGF-like domain, RACE PCR was performed on clones, isolated from both spinal and cerebellum mRNA libraries, to obtain sequencing data from the EGF-like domain to the transmembrane domain. SEQ ID NOS. 26–31 present the corresponding amino acid sequences determined for several of these clones. One striking feature, seen in clones from each of the spinal cord and cerebellum libraries, was the presence of a stop codon in the EGF-like domain. For example, the clone C-119 (SEQ ID NO. 27) and S-93 (SEQ ID NO. 29) each have a stop codon in place of the codon for the C5 cyteine of the EGF-like domain (See FIG. 3). While the role of such a variant is not yet fully elucidated, it is possible that these variants represent a soluble form of ARIA (e.g. no transmembrane or cytoplasmic domains) that acts antagonistically to ARIA possessing a full EGF-like domain.

EXAMPLE NINE

In Situ hybridization with nucleotide probes directed to ARIA sequences

Tissues were fixed with 4% paraformaldeyhyde in PBS either by immersion (in the case of embryos) or perfusion (in the case of adults). Tissues were then slowly dehydrated and embedded in paraffin. Tissue sections (7–9 µm) were collected on gelatinized glass microscope slides. The procedures used for section treatment, hybridizations and washing were as described in Sasson et al (1988) *Development* 104:155–164. Hybridization was carried out at 52° C. for approximately 16 hr in 50% deionized formamide, 0.3 M sodium chloride, 20 mM TRIS-HCl (pH 7.4), mM EDTA, 10 mM $NaPO_4$ (pH 8), 10% dextran sulfate, 1 x Denhardt's solution, 50 µg/ml total yeast RNA with $3 \times 10^4$ cpm/µl $^{35}$S-labeled RNA probe under siliconized coverslips. Following hybridizations, coverslips were floated off in 5 x SSC, 10 mM dithiothreitol at 50° C., and washed in 50% formamide, 2 x SSC, 10 mM dithiothreitol at 65° C. Slides were then rinsed in washing buffer, treated with RNAse A (20 µg/ml; SIGMA), and washed at 37° C. for 15 min in 2 x SSC and then for 15 min in 0.1 x SSC. Sections were dehydrated rapidly, processed for autoradiography using NTB-2 Kodak emulsion, exposed for 4–28 days at 4° C., and examined using both light and dark field illumination under a microscope.

Chicken ARIA mRNA was identified using a 329 nt fragment corresponding to nt 15–344 of the chick ARIA cDNA (SEQ ID NO. 1) as the hybridization probe. The rat probes were similarly derived from the PCR synthesized cDNA (SEQ ID NO. 3) described in Example Seven. The original rat B1-1 was cleaved with Sph I generating two fragments, one of which ("the Ig probe") corresponds to the 5' end of the B1-1 clone up to the end of the sequence that encodes the Ig-like domain. The second fragment ("the EGF probe") extends from the beginning of the spacer domain and ends within the sequence of the transmembrane region as defined by the original PCR primers.

All of the above-cited references and publications are hereby incorporated by reference.

Equivalents

Those skilled in the art will recognize, or be able to ascertain, by no more than routine experimentation, many equivalents of the specific embodiments of the invention described herein. Such equivalents are intended to be encompassed by the following claims.

We claim:

1. An isolated neurotrophic polypeptide comprising an amino acid sequence selected from the group consisting of SEQ ID Nos. 4, 33, 35, and 36, which neurotrophic factor induces the formation of nicotinic acetylcholine receptors in a surface membrane of a cell.

2. The neurotrophic polypeptide of claim 1, wherein the neurotrophic polypeptide is a glycoprotein.

3. The neurotrophic polypeptide of claim 1, which neurotrophic polypeptide is produced by recombinant DNA techniques.

4. The neurotrophic polypeptide of claim 1, which neurotrophic polypeptide comprises the amino acid sequence of SEQ ID No. 4.

5. The neurotrophic polypeptide of claim 1, which neurotrophic polypeptide comprises the amino acid sequence of SEQ ID No. 33.

6. The neurotrophic polypeptide of claim 1, which neurotrophic polypeptide comprises the amino acid sequence of SEQ ID No. 35.

7. The neurotrophic polypeptide of claim 1, which neurotrophic polypeptide comprises the amino acid sequence of SEQ ID No. 36.

8. The neurotrophic polypeptide of claim 1, which neurotrophic polypeptide is fused to a second polypeptide sequence.

9. An isolated neurotrophic polypeptide comprising the amino acid sequence of SEQ ID. No. 2, which neurotrophic polypeptide induces the formation of nicotinic acetylcholine receptors in a surface membrane of a cell, and includes less than 20% by dry weight of chicken prion-like protein.

10. An isolated neurotrophic polypeptide comprising amino acid residues Cys141-Cys180 of SEQ ID. No. 2, which neurotrophic polypeptide induces the formation of nicotinic acetylcholine receptors in a surface membrane of a cell, and includes less than 20% by dry weight of chicken prion-like protein.

11. An isolated neurotrophic polypeptide comprising an EGF-like domain comprising amino acids 143–187 of SEQ ID NO: 4.

12. The neurotrophic polypeptide of claim 11, which neurotrophic polypeptide is fused to a second polypeptide sequence.

* * * * *

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 2351 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 23..1831

( x i ) SEQUENCE DESCRIPTION: SEQ ID NO:1:

```
GAATTCCGGC GTCCTGCGGG GG ATG TGG GCC ACC TCT GAA GGT CCA CTT CAG         52
                        Met Trp Ala Thr Ser Glu Gly Pro Leu Gln
                         1               5                   10

TAC AGC CTG GCA CCA ACA CAG ACG GAC GTC AAC AGC AGT TAC AGC ACA         100
Tyr Ser Leu Ala Pro Thr Gln Thr Asp Val Asn Ser Ser Tyr Ser Thr
                 15                  20                  25

GTG CCT CCC AAA TTG AAG GAA ATG GAA AAC CAA GAG GTT GCT GTG GGT         148
Val Pro Pro Lys Leu Lys Glu Met Glu Asn Gln Glu Val Ala Val Gly
             30                  35                  40

CAG AAG CTA GTG CTA AGG TGT GAA ACC ACT TCA GAG TAC CCT GCG CTC         196
Gln Lys Leu Val Leu Arg Cys Glu Thr Thr Ser Glu Tyr Pro Ala Leu
             45                  50                  55

AGA TTC AAA TGG TTA AAG AAC GGG AAG GAA ATA ACG AAA AAA AAC AGA         244
Arg Phe Lys Trp Leu Lys Asn Gly Lys Glu Ile Thr Lys Lys Asn Arg
         60                  65                  70

CCC GAA AAT GTC AAG ATC CCC AAA AAG CAA AAG AAA TAC TCT GAG CTT         292
Pro Glu Asn Val Lys Ile Pro Lys Lys Gln Lys Lys Tyr Ser Glu Leu
 75                  80                  85                  90

CAT ATT TAT AGG GCC ACG TTG GCT GAC GCT GGG GAA TAC GCA TGC AGA         340
His Ile Tyr Arg Ala Thr Leu Ala Asp Ala Gly Glu Tyr Ala Cys Arg
                 95                 100                 105

GTG AGC AGC AAA CTA GGG AAC GAC AGT ACT AAA GCA AGT GTT ATC ATC         388
Val Ser Ser Lys Leu Gly Asn Asp Ser Thr Lys Ala Ser Val Ile Ile
            110                 115                 120

ACA GAC ACC AAT GCC ACT TCT ACA TCT ACA ACT GGG ACA AGT CAT CTC         436
Thr Asp Thr Asn Ala Thr Ser Thr Ser Thr Thr Gly Thr Ser His Leu
            125                 130                 135

ACA AAA TGT GAC ATA AAG CAG AAA GCC TTC TGT GTA AAT GGG GGA GAG         484
Thr Lys Cys Asp Ile Lys Gln Lys Ala Phe Cys Val Asn Gly Gly Glu
    140                 145                 150

TGC TAC ATG GTT AAA GAC CTC CCA AAC CCT CCA CGA TAC CTA TGC AGG         532
```

```
Cys Tyr Met Val Lys Asp Leu Pro Asn Pro Pro Arg Tyr Leu Cys Arg
155                 160             165                 170

TGC CCA AAT GAA TTT ACT GGT GAT CGC TGC CAA AAC TAC GTA ATG GCC    580
Cys Pro Asn Glu Phe Thr Gly Asp Arg Cys Gln Asn Tyr Val Met Ala
            175                 180                 185

AGC TTC TAC AAG CAT CTT GGG ATT GAA TTT ATG GAA GCT GAG GAA CTG    628
Ser Phe Tyr Lys His Leu Gly Ile Glu Phe Met Glu Ala Glu Glu Leu
                190                 195                 200

TAC CAG AAA CGG GTG CTG ACC ATA ACT GGC ATT TGC ATT GCT CTT CTA    676
Tyr Gln Lys Arg Val Leu Thr Ile Thr Gly Ile Cys Ile Ala Leu Leu
            205                 210                 215

GTA GTT GGC ATC ATG TGT GTG GTG GCC TAC TGC AAA ACC AAG AAG CAG    724
Val Val Gly Ile Met Cys Val Val Ala Tyr Cys Lys Thr Lys Lys Gln
    220                 225                 230

AGG AAA AAG TTG CAT GAC CGC CTT CGG CAG AGC CTT CGC TCA GAG AGG    772
Arg Lys Lys Leu His Asp Arg Leu Arg Gln Ser Leu Arg Ser Glu Arg
235                 240                 245                 250

AAC AAC GTT ATG AAC ATG GCA AAT GGG CCA CAC CAC CCC AAC CCA CCA    820
Asn Asn Val Met Asn Met Ala Asn Gly Pro His His Pro Asn Pro Pro
                255                 260                 265

CCA GAC AAT GTC CAG CTG GTG AAT CAG TAC GTT TCA AAA AAC ATA ATC    868
Pro Asp Asn Val Gln Leu Val Asn Gln Tyr Val Ser Lys Asn Ile Ile
            270                 275                 280

TCC AGT GAA CGT GTC GTT GAG CGA GAA ACC GAG ACC TCG TTT TCC ACA    916
Ser Ser Glu Arg Val Val Glu Arg Glu Thr Glu Thr Ser Phe Ser Thr
                285                 290                 295

AGC CAC TAC ACC TCA ACA ACT CAT CAC TCC ATG ACA GTC ACC CAG ACG    964
Ser His Tyr Thr Ser Thr Thr His His Ser Met Thr Val Thr Gln Thr
        300                 305                 310

CCT AGC CAC AGC TGG AGT AAT GGC CAT ACC GAA AGC ATT CTC TCC GAA    1012
Pro Ser His Ser Trp Ser Asn Gly His Thr Glu Ser Ile Leu Ser Glu
315                 320                 325                 330

AGC CAC TCC GTG CTC GTC AGC TCC TCA GTG GAG AAT AGC AGG CAC ACC    1060
Ser His Ser Val Leu Val Ser Ser Ser Val Glu Asn Ser Arg His Thr
                335                 340                 345

AGC CCA ACA GGG CCA CGA GGC CGC CTC AAT GGN ATT GGT GGG CCA AGG    1108
Ser Pro Thr Gly Pro Arg Gly Arg Leu Asn Gly Ile Gly Gly Pro Arg
            350                 355                 360

GAA GGC AAC AGC TTC CTC CGG CAT GCA AGA GAG ACC CCT GAC TCC TAC    1156
Glu Gly Asn Ser Phe Leu Arg His Ala Arg Glu Thr Pro Asp Ser Tyr
                365                 370                 375

CGA GAC TCT CCT CAC AGT GAA AGG TAT GTC TCA GCT ATG ACC ACA CCA    1204
Arg Asp Ser Pro His Ser Glu Arg Tyr Val Ser Ala Met Thr Thr Pro
            380                 385                 390

GCT CGC ATG TCA CCC GTT GAT TTC CAC ACT CCA ACT TCT CCC AAG TCC    1252
Ala Arg Met Ser Pro Val Asp Phe His Thr Pro Thr Ser Pro Lys Ser
395                 400                 405                 410

CCT CCA TCT GAA ATG TCA CCA CCA GTT TCC AGC TTG ACC ATC TCC ATC    1300
Pro Pro Ser Glu Met Ser Pro Pro Val Ser Ser Leu Thr Ile Ser Ile
                415                 420                 425

CCT TCG GTG GCG GTG AGT CCC TTT ATG GAC GAG GAG AGA CCG CTG CTG    1348
Pro Ser Val Ala Val Ser Pro Phe Met Asp Glu Glu Arg Pro Leu Leu
            430                 435                 440

TTG GTG ACC CCA CCA CGG CTG CGT GAG AAG TAC GAC AAC CAC CTT CAG    1396
Leu Val Thr Pro Pro Arg Leu Arg Glu Lys Tyr Asp Asn His Leu Gln
        445                 450                 455

CAA TTC AAC TCC TTC CAC AAC AAT CCC ACC CAT GAG AGC AAC AGT CTG    1444
Gln Phe Asn Ser Phe His Asn Asn Pro Thr His Glu Ser Asn Ser Leu
    460                 465                 470

CCA CCC AGT CCT CTG AGG ATA GTG GAG GAT GAA GAG TAT GAG ACC ACG    1492
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Pro | Pro | Ser | Pro | Leu | Arg | Ile | Val | Glu | Asp | Glu | Glu | Tyr | Glu | Thr | Thr | |
| 475 | | | | 480 | | | | 485 | | | | | | 490 | | |
| CAG | GAG | TAC | GAA | CCA | GCA | CAG | GAG | CCT | CCA | AAG | AAA | CTC | ACC | AAC | AGC | 1540 |
| Gln | Glu | Tyr | Glu | Pro | Ala | Gln | Glu | Pro | Pro | Lys | Lys | Leu | Thr | Asn | Ser | |
| | | | | 495 | | | | 500 | | | | | | 505 | | |
| CGG | AGG | GTG | AAA | AGA | ACA | AAG | CCC | AAT | GGC | CAT | ATT | TCC | AGC | AGG | GTA | 1588 |
| Arg | Arg | Val | Lys | Arg | Thr | Lys | Pro | Asn | Gly | His | Ile | Ser | Ser | Arg | Val | |
| | | | 510 | | | | | 515 | | | | | 520 | | | |
| GAA | GTG | GAC | TCC | GAC | ACA | AGC | TCT | CAG | AGC | ACT | AGC | TCT | GAG | AGC | GAA | 1636 |
| Glu | Val | Asp | Ser | Asp | Thr | Ser | Ser | Gln | Ser | Thr | Ser | Ser | Glu | Ser | Glu | |
| | | 525 | | | | | 530 | | | | | 535 | | | | |
| ACA | GAA | GAT | GAA | AGA | ATA | GGT | GAG | GAT | ACA | CCA | TTT | CTT | AGC | ATA | CAA | 1684 |
| Thr | Glu | Asp | Glu | Arg | Ile | Gly | Glu | Asp | Thr | Pro | Phe | Leu | Ser | Ile | Gln | |
| 540 | | | | | 545 | | | | | 550 | | | | | | |
| AAT | CCC | ATG | NCA | ACC | AGT | CTG | GAG | CCA | GCC | TCT | GCA | TAT | CGG | CTG | GCT | 1732 |
| Asn | Pro | Met | Xaa | Thr | Ser | Leu | Glu | Pro | Ala | Ser | Ala | Tyr | Arg | Leu | Ala | |
| 555 | | | | | 560 | | | | | 565 | | | | | 570 | |
| GAG | AAC | AGG | ACT | AAC | CCG | NCA | AAT | CGC | TTC | TCC | ACA | CCA | GAA | GAG | TTG | 1780 |
| Glu | Asn | Arg | Thr | Asn | Pro | Xaa | Asn | Arg | Phe | Ser | Thr | Pro | Glu | Glu | Leu | |
| | | | | 575 | | | | | 580 | | | | | 585 | | |
| CAA | GCA | AGG | TTG | TCC | AGT | GTA | ATA | GCT | AAC | CAA | GAC | CCT | ATT | GCT | GTA | 1828 |
| Gln | Ala | Arg | Leu | Ser | Ser | Val | Ile | Ala | Asn | Gln | Asp | Pro | Ile | Ala | Val | |
| | | | | 590 | | | | | 595 | | | | | 600 | | |

```
TAAGACATAA ACAAAACACA TAGATTCACA TGTAAAACTT TATTTTATAT AATGAAGTAT       1888
TCCACCTTTA AATTAAACAA TTTATTTTAT TTAGCAATT  CCGCTGATAG AAAACAAGAG       1948
TGGAAAAAGA AACTTTTATA AATTAAGTAT ACGTATGTAC AAATGTGTTA TGTGCCATAT       2008
GTAGCAATTT TTTACAGTAT TTCCAAAATG GGGAAAGATA TCAATGGTGC CTTTATGTTA       2068
TGTTATGTTG AGAGCAAGTT TTGTACAGCT ACAATGATTG CTGTCCCGTA GTATTTTGCA       2128
AAACCTTCTA GCCCTCAGTT GTTCTGGCTT TTTTGTGCAT TGCATTATAA TGACTGGATG       2188
TATGATTTGC AAGAATTGCA GAAGTCCCCA TTTGCTTGTT GTGGAANCCC CAGATCAAAA       2248
AGCCCTGTTA TGGCACTCAC ACCCTATCCA CTTCACCAGG AAAAAAAAAA AATCAAAAAA       2308
AAAAAAAAAA AAAAAAGAA  AAAAAAAAAA AAAAAGGAAT TCC                         2351
```

( 2 ) INFORMATION FOR SEQ ID NO:2:

( i ) SEQUENCE CHARACTERISTICS:
        ( A ) LENGTH: 602 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
| --- | --- | --- | --- | --- | --- | --- | --- | --- | --- | --- | --- | --- | --- | --- |
| Met | Trp | Ala | Thr | Ser | Glu | Gly | Pro | Leu | Gln | Tyr | Ser | Leu | Ala | Pro | Thr |
| 1 | | | | 5 | | | | | 10 | | | | | 15 | |
| Gln | Thr | Asp | Val | Asn | Ser | Ser | Tyr | Ser | Thr | Val | Pro | Pro | Lys | Leu | Lys |
| | | | 20 | | | | 25 | | | | | 30 | | | |
| Glu | Met | Glu | Asn | Gln | Glu | Val | Ala | Val | Gly | Gln | Lys | Leu | Val | Leu | Arg |
| | | 35 | | | | 40 | | | | | 45 | | | | |
| Cys | Glu | Thr | Thr | Ser | Glu | Tyr | Pro | Ala | Leu | Arg | Phe | Lys | Trp | Leu | Lys |
| | 50 | | | | | 55 | | | | 60 | | | | | |
| Asn | Gly | Lys | Glu | Ile | Thr | Lys | Lys | Asn | Arg | Pro | Glu | Asn | Val | Lys | Ile |
| 65 | | | | | 70 | | | | 75 | | | | | 80 | |
| Pro | Lys | Lys | Gln | Lys | Lys | Tyr | Ser | Glu | Leu | His | Ile | Tyr | Arg | Ala | Thr |
| | | | | 85 | | | | | 90 | | | | | 95 | |
| Leu | Ala | Asp | Ala | Gly | Glu | Tyr | Ala | Cys | Arg | Val | Ser | Ser | Lys | Leu | Gly |

|     |     |     | 100 |     |     |     | 105 |     |     |     | 110 |     |     |     |
|-----|-----|-----|-----|-----|-----|-----|-----|-----|-----|-----|-----|-----|-----|-----|
| Asn | Asp | Ser | Thr | Lys | Ala | Ser | Val | Ile | Ile | Thr | Asp | Thr | Asn | Ala | Thr |
|     |     |     | 115 |     |     |     | 120 |     |     |     | 125 |     |     |     |
| Ser | Thr | Ser | Thr | Thr | Gly | Thr | Ser | His | Leu | Thr | Lys | Cys | Asp | Ile | Lys |
|     |     |     | 130 |     |     |     | 135 |     |     |     | 140 |     |     |     |
| Gln | Lys | Ala | Phe | Cys | Val | Asn | Gly | Gly | Glu | Cys | Tyr | Met | Val | Lys | Asp |
| 145 |     |     |     |     | 150 |     |     |     |     | 155 |     |     |     |     | 160 |
| Leu | Pro | Asn | Pro | Pro | Arg | Tyr | Leu | Cys | Arg | Cys | Pro | Asn | Glu | Phe | Thr |
|     |     |     |     | 165 |     |     |     |     | 170 |     |     |     |     | 175 |     |
| Gly | Asp | Arg | Cys | Gln | Asn | Tyr | Val | Met | Ala | Ser | Phe | Tyr | Lys | His | Leu |
|     |     |     | 180 |     |     |     |     | 185 |     |     |     |     | 190 |     |     |
| Gly | Ile | Glu | Phe | Met | Glu | Ala | Glu | Glu | Leu | Tyr | Gln | Lys | Arg | Val | Leu |
|     |     |     | 195 |     |     |     | 200 |     |     |     |     | 205 |     |     |     |
| Thr | Ile | Thr | Gly | Ile | Cys | Ile | Ala | Leu | Leu | Val | Val | Gly | Ile | Met | Cys |
|     | 210 |     |     |     |     | 215 |     |     |     |     |     | 220 |     |     |     |
| Val | Val | Ala | Tyr | Cys | Lys | Thr | Lys | Lys | Gln | Arg | Lys | Lys | Leu | His | Asp |
| 225 |     |     |     |     | 230 |     |     |     |     | 235 |     |     |     |     | 240 |
| Arg | Leu | Arg | Gln | Ser | Leu | Arg | Ser | Glu | Arg | Asn | Asn | Val | Met | Asn | Met |
|     |     |     |     | 245 |     |     |     |     | 250 |     |     |     |     | 255 |     |
| Ala | Asn | Gly | Pro | His | His | Pro | Asn | Pro | Pro | Asp | Asn | Val | Gln | Leu |     |
|     |     |     | 260 |     |     |     |     | 265 |     |     |     |     | 270 |     |     |
| Val | Asn | Gln | Tyr | Val | Ser | Lys | Asn | Ile | Ile | Ser | Ser | Glu | Arg | Val | Val |
|     |     |     | 275 |     |     |     |     | 280 |     |     |     |     | 285 |     |     |
| Glu | Arg | Glu | Thr | Glu | Thr | Ser | Phe | Ser | Thr | Ser | His | Tyr | Thr | Ser | Thr |
|     |     |     | 290 |     |     |     | 295 |     |     |     |     | 300 |     |     |     |
| Thr | His | His | Ser | Met | Thr | Val | Thr | Gln | Thr | Pro | Ser | His | Ser | Trp | Ser |
| 305 |     |     |     |     |     | 310 |     |     |     |     | 315 |     |     |     | 320 |
| Asn | Gly | His | Thr | Glu | Ser | Ile | Leu | Ser | Glu | Ser | His | Ser | Val | Leu | Val |
|     |     |     |     | 325 |     |     |     |     | 330 |     |     |     |     | 335 |     |
| Ser | Ser | Ser | Val | Glu | Asn | Ser | Arg | His | Thr | Ser | Pro | Thr | Gly | Pro | Arg |
|     |     |     | 340 |     |     |     |     | 345 |     |     |     |     | 350 |     |     |
| Gly | Arg | Leu | Asn | Gly | Ile | Gly | Gly | Pro | Arg | Glu | Gly | Asn | Ser | Phe | Leu |
|     |     |     | 355 |     |     |     |     | 360 |     |     |     |     | 365 |     |     |
| Arg | His | Ala | Arg | Glu | Thr | Pro | Asp | Ser | Tyr | Arg | Asp | Ser | Pro | His | Ser |
|     |     |     | 370 |     |     |     |     | 375 |     |     |     |     | 380 |     |     |
| Glu | Arg | Tyr | Val | Ser | Ala | Met | Thr | Thr | Pro | Ala | Arg | Met | Ser | Pro | Val |
| 385 |     |     |     |     |     | 390 |     |     |     |     | 395 |     |     |     | 400 |
| Asp | Phe | His | Thr | Pro | Thr | Ser | Pro | Lys | Ser | Pro | Pro | Ser | Glu | Met | Ser |
|     |     |     |     | 405 |     |     |     |     | 410 |     |     |     |     | 415 |     |
| Pro | Pro | Val | Ser | Ser | Leu | Thr | Ile | Ser | Ile | Pro | Ser | Val | Ala | Val | Ser |
|     |     |     | 420 |     |     |     |     | 425 |     |     |     |     | 430 |     |     |
| Pro | Phe | Met | Asp | Glu | Glu | Arg | Pro | Leu | Leu | Leu | Val | Thr | Pro | Pro | Arg |
|     |     |     | 435 |     |     |     |     | 440 |     |     |     |     | 445 |     |     |
| Leu | Arg | Glu | Lys | Tyr | Asp | Asn | His | Leu | Gln | Gln | Phe | Asn | Ser | Phe | His |
|     | 450 |     |     |     |     | 455 |     |     |     |     | 460 |     |     |     |     |
| Asn | Asn | Pro | Thr | His | Glu | Ser | Asn | Ser | Leu | Pro | Pro | Ser | Pro | Leu | Arg |
| 465 |     |     |     |     | 470 |     |     |     |     | 475 |     |     |     |     | 480 |
| Ile | Val | Glu | Asp | Glu | Glu | Tyr | Glu | Thr | Thr | Gln | Glu | Tyr | Glu | Pro | Ala |
|     |     |     |     | 485 |     |     |     |     | 490 |     |     |     |     | 495 |     |
| Gln | Glu | Pro | Pro | Lys | Lys | Leu | Thr | Asn | Ser | Arg | Arg | Val | Lys | Arg | Thr |
|     |     |     | 500 |     |     |     |     | 505 |     |     |     |     | 510 |     |     |
| Lys | Pro | Asn | Gly | His | Ile | Ser | Ser | Arg | Val | Glu | Val | Asp | Ser | Asp | Thr |
|     |     |     | 515 |     |     |     |     | 520 |     |     |     |     | 525 |     |     |

| | | | | | | | | | | | | | | |
|---|---|---|---|---|---|---|---|---|---|---|---|---|---|---|
| Ser | Ser | Gln | Ser | Thr | Ser | Ser | Glu | Ser | Glu | Thr | Glu | Asp | Glu | Arg | Ile |
| | 530 | | | | | 535 | | | | 540 | | | | | |
| Gly | Glu | Asp | Thr | Pro | Phe | Leu | Ser | Ile | Gln | Asn | Pro | Met | Thr | Thr | Ser |
| 545 | | | | | 550 | | | | 555 | | | | | | 560 |
| Leu | Glu | Pro | Ala | Ser | Ala | Tyr | Arg | Leu | Ala | Glu | Asn | Arg | Thr | Asn | Pro |
| | | | | 565 | | | | | 570 | | | | | 575 | |
| Thr | Asn | Arg | Phe | Ser | Thr | Pro | Glu | Glu | Leu | Gln | Ala | Arg | Leu | Ser | Ser |
| | | | 580 | | | | | 585 | | | | | 590 | | |
| Val | Ile | Ala | Asn | Gln | Asp | Pro | Ile | Ala | Val | | | | | | |
| | | | 595 | | | | 600 | | | | | | | | |

( 2 ) INFORMATION FOR SEQ ID NO:3:

( i ) SEQUENCE CHARACTERISTICS:
        ( A ) LENGTH: 693 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..693

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| CCC | AGA | TTG | AAA | GAA | ATG | AAG | AGC | CAG | GAG | TCA | GCT | GCA | GGC | TCC | AAG | 48 |
| Pro | Arg | Leu | Lys | Glu | Met | Lys | Ser | Gln | Glu | Ser | Ala | Ala | Gly | Ser | Lys | |
| 1 | | | | 5 | | | | | 10 | | | | | 15 | | |
| CTA | GTG | CTC | CGG | TGC | GAA | ACC | AGC | TCC | GAG | TAC | TCC | TCA | CTC | AGA | TTC | 96 |
| Leu | Val | Leu | Arg | Cys | Glu | Thr | Ser | Ser | Glu | Tyr | Ser | Ser | Leu | Arg | Phe | |
| | | | 20 | | | | | 25 | | | | | 30 | | | |
| AAA | TGG | TTC | AAG | AAT | GGG | AAC | GAG | CTG | AAC | CGC | AAA | AAT | AAA | CCA | GAA | 144 |
| Lys | Trp | Phe | Lys | Asn | Gly | Asn | Glu | Leu | Asn | Arg | Lys | Asn | Lys | Pro | Glu | |
| | | 35 | | | | | 40 | | | | | 45 | | | | |
| AAC | ATC | AAG | ATA | CAG | AAC | AAG | CCA | GGG | AAG | TCA | GAG | CTT | CGA | ATT | AAC | 192 |
| Asn | Ile | Lys | Ile | Gln | Asn | Lys | Pro | Gly | Lys | Ser | Glu | Leu | Arg | Ile | Asn | |
| 50 | | | | | 55 | | | | | 60 | | | | | | |
| AAA | GCA | TCC | CTG | GCT | GAC | TCT | GGA | GAG | TAT | ATG | TGC | AAA | GTG | ATC | AGC | 240 |
| Lys | Ala | Ser | Leu | Ala | Asp | Ser | Gly | Glu | Tyr | Met | Cys | Lys | Val | Ile | Ser | |
| 65 | | | | | 70 | | | | | 75 | | | | | 80 | |
| AAG | TTA | GGA | AAT | GAC | AGT | GCC | TCT | GCC | AAC | ATC | ACC | ATT | GTT | GAG | TCA | 288 |
| Lys | Leu | Gly | Asn | Asp | Ser | Ala | Ser | Ala | Asn | Ile | Thr | Ile | Val | Glu | Ser | |
| | | | | 85 | | | | | 90 | | | | | 95 | | |
| AAC | GAG | TTC | ATC | ACT | GGC | ATG | CCA | GCC | TCG | ACT | GAG | ACA | GCC | TAT | GTG | 336 |
| Asn | Glu | Phe | Ile | Thr | Gly | Met | Pro | Ala | Ser | Thr | Glu | Thr | Ala | Tyr | Val | |
| | | | 100 | | | | | 105 | | | | | 110 | | | |
| TCC | TCA | GAG | TCT | CCC | ATT | AGA | ATC | TCA | GTT | TCA | ACA | GAA | GGC | GCA | AAC | 384 |
| Ser | Ser | Glu | Ser | Pro | Ile | Arg | Ile | Ser | Val | Ser | Thr | Glu | Gly | Ala | Asn | |
| | | 115 | | | | | 120 | | | | | 125 | | | | |
| ACT | TCT | TCA | TCC | ACA | TCA | ACA | TCC | ACG | ACT | GGG | ACC | AGC | CAT | CTC | ATA | 432 |
| Thr | Ser | Ser | Ser | Thr | Ser | Thr | Ser | Thr | Thr | Gly | Thr | Ser | His | Leu | Ile | |
| | 130 | | | | | 135 | | | | | 140 | | | | | |
| AAG | TGT | GCG | GAG | AAG | GAG | AAA | ACT | TTC | TGT | GTG | AAT | GGG | GGC | GAG | TGC | 480 |
| Lys | Cys | Ala | Glu | Lys | Glu | Lys | Thr | Phe | Cys | Val | Asn | Gly | Gly | Glu | Cys | |
| 145 | | | | | 150 | | | | | 155 | | | | | 160 | |
| TTC | ACG | GTG | AAG | GAC | CTG | TCA | AAC | CCG | TCA | AGA | TCC | TTG | TGC | AAG | TGC | 528 |
| Phe | Thr | Val | Lys | Asp | Leu | Ser | Asn | Pro | Ser | Arg | Ser | Leu | Cys | Lys | Cys | |
| | | | | 165 | | | | | 170 | | | | | 175 | | |
| CCA | AAT | GAG | TTT | ACT | GGT | GAT | CGT | TGC | CAA | AAC | TAC | GTA | ATG | GCC | AGC | 576 |
| Pro | Asn | Glu | Phe | Thr | Gly | Asp | Arg | Cys | Gln | Asn | Tyr | Val | Met | Ala | Ser | |
| | | | 180 | | | | | 185 | | | | | 190 | | | |

```
TTC  TAC  AAG  CAT  CTT  GGG  ATT  GAA  TTT  ATG  GAA  GCG  GAG  GAA  CTC  TAC        624
Phe  Tyr  Lys  His  Leu  Gly  Ile  Glu  Phe  Met  Glu  Ala  Glu  Glu  Leu  Tyr
          195                      200                     205

CAG  AAG  AGG  GTG  CTG  ACA  ATT  ACT  GGC  ATC  TGT  ATC  GCC  CTG  CTG  GTG        672
Gln  Lys  Arg  Val  Leu  Thr  Ile  Thr  Gly  Ile  Cys  Ile  Ala  Leu  Leu  Val
          210                      215                     220

GTC  GGC  ATC  ATG  TGT  GTG  GTG                                                     693
Val  Gly  Ile  Met  Cys  Val  Val
225                      230
```

( 2 ) INFORMATION FOR SEQ ID NO:4:

( i ) SEQUENCE CHARACTERISTICS:
        ( A ) LENGTH: 231 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Arg  Leu  Lys  Glu  Met  Lys  Ser  Gln  Glu  Ser  Ala  Ala  Gly  Ser  Lys
 1                    5                        10                      15

Leu  Val  Leu  Arg  Cys  Glu  Thr  Ser  Ser  Glu  Tyr  Ser  Ser  Leu  Arg  Phe
               20                       25                       30

Lys  Trp  Phe  Lys  Asn  Gly  Asn  Glu  Leu  Asn  Arg  Lys  Asn  Lys  Pro  Glu
          35                      40                       45

Asn  Ile  Lys  Ile  Gln  Asn  Lys  Pro  Gly  Lys  Ser  Glu  Leu  Arg  Ile  Asn
     50                      55                       60

Lys  Ala  Ser  Leu  Ala  Asp  Ser  Gly  Glu  Tyr  Met  Cys  Lys  Val  Ile  Ser
65                       70                       75                       80

Lys  Leu  Gly  Asn  Asp  Ser  Ala  Ser  Ala  Asn  Ile  Thr  Ile  Val  Glu  Ser
                    85                       90                       95

Asn  Glu  Phe  Ile  Thr  Gly  Met  Pro  Ala  Ser  Thr  Glu  Thr  Ala  Tyr  Val
                    100                     105                     110

Ser  Ser  Glu  Ser  Pro  Ile  Arg  Ile  Ser  Val  Ser  Thr  Glu  Gly  Ala  Asn
          115                     120                     125

Thr  Ser  Ser  Ser  Thr  Ser  Thr  Thr  Gly  Thr  Ser  His  Leu  Ile
     130                     135                     140

Lys  Cys  Ala  Glu  Lys  Glu  Lys  Thr  Phe  Cys  Val  Asn  Gly  Gly  Glu  Cys
145                     150                     155                     160

Phe  Thr  Val  Lys  Asp  Leu  Ser  Asn  Pro  Ser  Arg  Ser  Leu  Cys  Lys  Cys
                    165                     170                     175

Pro  Asn  Glu  Phe  Thr  Gly  Asp  Arg  Cys  Gln  Asn  Tyr  Val  Met  Ala  Ser
               180                     185                     190

Phe  Tyr  Lys  His  Leu  Gly  Ile  Glu  Phe  Met  Glu  Ala  Glu  Glu  Leu  Tyr
          195                     200                     205

Gln  Lys  Arg  Val  Leu  Thr  Ile  Thr  Gly  Ile  Cys  Ile  Ala  Leu  Leu  Val
          210                     215                     220

Val  Gly  Ile  Met  Cys  Val  Val
225                     230
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

Asn Arg Pro Glu Asn Val Lys
1               5

( 2 ) INFORMATION FOR SEQ ID NO:6:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:6:

Ala Thr Leu Ala Asp Ala Gly Glu Tyr Ala Cys Arg
1               5                   10

( 2 ) INFORMATION FOR SEQ ID NO:7:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:7:

GCCGARAA Y G TNAAG                                                      15

( 2 ) INFORMATION FOR SEQ ID NO:8:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:8:

CKRCAGCRTA Y TCNCC                                                      16

( 2 ) INFORMATION FOR SEQ ID NO:9:

( i ) SEQUENCE CHARACTERISTICS:
      ( A ) LENGTH: 97 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

GGCCCGGAAA TGTCAAGATC CCCAAAAAGC AAAAGAAATA CTCTGAGCTT CATATTTATA       60

GAGCCACGTT GGCTGACGCT GGGGAATACG CCTGCCG                                97

( 2 ) INFORMATION FOR SEQ ID NO:10:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:10:

GCGCAAACAC TTCTTCATCC AC 22

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

Gly Ala Asn Thr Ser Ser Ser Thr
1               5

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CACCACACAC ATGATGCCGA C 21

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

Val Gly Ile Met Cys Val Val
1               5

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CACGACTAGT ACTAGCCATC TC 22

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CGACAAGCTT CTAGTAGAGT TCC 23

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CATTTTACCT TTCGCTATGA GGAG 24

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GCGCAAACAC TTCTTCATCC AC 22

( 2 ) INFORMATION FOR SEQ ID NO:18:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CTCATCTTCG GCGAGATGTC TG 22

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TGCAAAGTGA TCAGCAAGTT AGG 23

( 2 ) INFORMATION FOR SEQ ID NO:20:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:20:

Thr Lys Ala Ser Val Ile Ile Thr Asp Thr Asn Ala
1              5                          10

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

CAGATTGAAA GAAATGAAGA GCC         23

( 2 ) INFORMATION FOR SEQ ID NO:22:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Cys Asp Ile Lys Gln Lys Ala Phe Cys Val Asn Gly Gly Glu Cys Tyr
 1               5                  10                  15

Met Val Lys Asp Leu Pro Asn Pro Arg Tyr Leu Cys Arg Cys Pro
         20                  25                  30

Asn Glu Phe Thr Gly Asp Arg Cys
         35                  40

( 2 ) INFORMATION FOR SEQ ID NO:23:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 2
        ( D ) OTHER INFORMATION: /label=Z
            / note= "Z represents 4 to 14 amino acid residues
            which can be the same or different"

( i x ) FEATURE:
        ( A ) NAME/KEY: Modified-site
        ( B ) LOCATION: 26
        ( D ) OTHER INFORMATION: /label=Y
            / note= "Y represents 8 to 14 amino acid residues
            which can be the same or different"

( x i ) SEQUENCE DESCRIPTION: SEQ ID NO:23:

Cys Xaa Cys Val Asn Gly Gly Xaa Cys Xaa Xaa Val Lys Asp Lys Xaa
 1               5                  10                  15

Xaa Pro Xaa Arg Tyr Leu Cys Xaa Cys Xaa Cys
         20                  25

( 2 ) INFORMATION FOR SEQ ID NO:24:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Met Trp Ala Thr Ser Glu Gly Pro Leu Gln Tyr Ser Leu Ala Pro Thr
1               5                   10                  15

Glu Thr Asp Val Ser Ser Tyr Asn Thr Val
            20              25

( 2 ) INFORMATION FOR SEQ ID NO:25:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:25:

Cys Xaa Xaa Xaa Xaa Xaa Xaa Xaa Cys Xaa Xaa Xaa Gly Xaa Cys Xaa
1               5                   10                  15

Xaa Xaa Xaa Xaa Xaa Xaa Xaa Xaa Xaa Xaa Xaa Xaa Cys Xaa Cys Xaa
            20                  25                  30

Xaa Xaa Xaa Xaa Gly Xaa Arg Cys
            35              40

( 2 ) INFORMATION FOR SEQ ID NO:26:

( i ) SEQUENCE CHARACTERISTICS:
        ( A ) LENGTH: 113 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:26:

Cys Asp Ile Lys Gln Lys Ala Phe Cys Val Asn Gly Gly Glu Cys Tyr
1               5                   10                  15

Met Val Lys Asp Leu Pro Asn Pro Arg Tyr Leu Cys Arg Cys Pro
            20                  25                  30

Asn Glu Phe Thr Gly Asp Arg Cys Gln Asn Tyr Val Met Gly Ser Phe
            35                  40                  45

Tyr Lys His Leu Gly Ile Glu Phe Met Glu Ala Glu Glu Leu Tyr Gln
        50                  55                  60

Lys Arg Val Leu Thr Ile Thr Gly Ile Cys Ile Ala Leu Leu Val Val
65                  70                  75                  80

Gly Ile Met Cys Val Val Ala Tyr Cys Lys Thr Lys Lys Glu Arg Lys
                85                  90                  95

Lys Leu His Asp Arg Leu Arg Gln Ser Leu Arg Ser Glu Arg Asn Asn
                100                 105                 110

Val ( 2 ) INFORMATION FOR SEQ ID NO:27:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:27:

Cys Asp Ile Lys Gln Lys Ala Phe Cys Val Asn Gly Gly Glu Cys Tyr
1               5                   10                  15

Met Val Lys Asp Leu Pro Asn Pro Pro Arg Tyr Leu Cys Arg
            20              25                  30

( 2 ) INFORMATION FOR SEQ ID NO:28:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:28:

Cys Asp Ile Lys Gln Lys Ala Phe Cys Val Asn Gly Gly Glu Cys Tyr
1               5                   10                  15

Met Val Lys Asp Leu Pro Ser Pro Pro Arg Tyr Leu Cys Arg Cys Ser
            20              25                  30

Asn Glu Phe Thr Gly Asp Arg Cys Gln Asn Tyr Val Met Ala Ser Phe
        35              40                  45

Tyr Lys His Leu Gly Ile Glu Phe Met Ala Glu Glu Leu Tyr Gln Lys
    50              55                  60

Arg Val Leu Thr Ile Thr Gly Ile Cys Ile Ala Leu Leu Val Val Gly
65                  70                  75                  80

Ile Met Cys Val Val Ala Tyr Cys Lys Thr Lys
                85                  90

( 2 ) INFORMATION FOR SEQ ID NO:29:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:29:

Cys Asp Ile Lys Gln Lys Ala Phe Cys Val Asn Gly Gly Glu Cys Tyr
1               5                   10                  15

Met Val Lys Asp Leu Pro Asn Pro Pro Arg Tyr Leu Cys Arg
            20              25                  30

( 2 ) INFORMATION FOR SEQ ID NO:30:

( i ) SEQUENCE CHARACTERISTICS:
        ( A ) LENGTH: 81 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:30:

```
        Cys  Asp  Ile  Lys  Gln  Lys  Ala  Phe  Cys  Val  Asn  Gly  Gly  Glu  Cys  Tyr
        1              5                        10                             15

Met  Val  Lys  Asp  Leu  Pro  Asn  Pro  Pro  Arg  Tyr  Leu  Cys  Arg  Cys  Pro
                       20                       25                      30

Asn  Glu  Phe  Thr  Gly  Asp  Arg  Cys  Gln  Asn  Tyr  Val  Met  Ala  Ser  Phe
                  35                      40                      45

Tyr  Lys  His  Leu  Gly  Ile  Glu  Phe  Met  Glu  Ala  Glu  Glu  Leu  Tyr  Gln
             50                       55                      60

Lys  Arg  Val  Leu  Thr  Ile  Thr  Gly  Ile  Cys  Ile  Ala  Gln  Gln  Gln  Ser
        65                       70                      75                            80

Lys
```

( 2 ) INFORMATION FOR SEQ ID NO:31:

( i ) SEQUENCE CHARACTERISTICS:
      ( A ) LENGTH: 83 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: internal ( x i ) SEQUENCE DESCRIPTION: SEQ ID NO:31:

```
        Cys  Asp  Ile  Lys  Gln  Lys  Ala  Phe  Cys  Val  Asn  Gly  Gly  Glu  Cys  Tyr
        1              5                        10                             15

Met  Val  Lys  Asp  Leu  Pro  Asn  Pro  Pro  Arg  Tyr  Leu  Cys  Arg  Cys  Pro
                       20                       25                      30

Asn  Glu  Phe  Thr  Gly  Asp  Arg  Cys  Gln  Asn  Tyr  Val  Met  Ala  Ser  Phe
                  35                      40                      45

Tyr  Lys  His  Leu  Gly  Ile  Glu  Phe  Met  Ala  Glu  Glu  Leu  Tyr  Gln  Lys
             50                       55                      60

Arg  Val  Leu  Thr  Ile  Thr  Gly  Ile  Cys  Ile  Ala  Leu  Leu  Val  Val  Gly
        65                       70                      75                            80

Ile  Met  Cys
```

( 2 ) INFORMATION FOR SEQ ID NO:32:

( i ) SEQUENCE CHARACTERISTICS:
      ( A ) LENGTH: 90 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: internal ( x i ) SEQUENCE DESCRIPTION: SEQ ID NO:32:

```
        Ser  Ala  Asn  Ile  Thr  Ile  Val  Glu  Ser  Asn  Ala  Thr  Ser  Thr  Ser  Thr
        1              5                        10                             15

Thr  Gly  Thr  Ser  His  Leu  Ile  Lys  Cys  Ala  Glu  Lys  Glu  Lys  Thr  Phe
                       20                       25                      30

Cys  Val  Asn  Gly  Gly  Glu  Cys  Phe  Thr  Val  Lys  Asp  Leu  Ser  Asn  Pro
                  35                      40                      45

Ser  Arg  Tyr  Leu  Cys  Lys  Cys  Pro  Asn  Glu  Phe  Thr  Gly  Asp  Arg  Cys
             50                       55                      60

Gln  Asn  Tyr  Val  Met  Ala  Ser  Phe  Tyr  Lys  His  Leu  Gly  Ile  Glu  Phe
        65                       70                      75                            80

Met  Glu  Ala  Glu  Glu  Leu  Tyr  Gln  Lys  Arg
```

(2) INFORMATION FOR SEQ ID NO:33:

(i) SEQUENCE CHARACTERISTICS:
       (A) LENGTH: 165 amino acids
       (B) TYPE: amino acid
       (C) STRANDEDNESS: single
       (D) TOPOLOGY: linear (ii) MOLECULE TYPE: peptide (v) FRAGMENT TYPE: internal (xi) SEQUENCE DESCRIPTION: SEQ ID NO:33:

```
Ala Gly Ser Lys Leu Val Leu Arg Cys Glu Thr Ser Ser Glu Tyr Ser
 1               5                  10                  15
Ser Leu Arg Phe Lys Trp Phe Lys Asn Gly Asn Glu Leu Asn Arg Arg
                20                  25                  30
Asn Lys Pro Glu Asn Ile Lys Ile Gln Lys Lys Pro Gly Lys Ser Glu
            35                  40                  45
Leu Arg Ile Asn Lys Ala Ser Leu Ala Asp Ser Gly Glu Tyr Met Cys
        50                  55                  60
Lys Val Ile Ser Lys Leu Gly Asn Asp Ser Ala Ser Ala Asn Ile Thr
 65                 70                  75                  80
Ile Val Glu Ser Asn Ala Thr Ser Thr Thr Gly Thr Ser His
                    85                  90                  95
Leu Ile Lys Cys Ala Glu Lys Glu Lys Thr Phe Cys Val Asn Gly Gly
                100                 105                 110
Glu Cys Phe Thr Val Lys Asp Leu Ser Asn Pro Ser Arg Tyr Leu Cys
            115                 120                 125
Lys Cys Pro Asn Glu Phe Thr Gly Asp Arg Cys Gln Asn Tyr Val Met
        130                 135                 140
Ala Ser Phe Tyr Lys His Leu Gly Ile Glu Phe Met Glu Ala Glu Glu
145                 150                 155                 160
Leu Tyr Gln Lys Arg
                165
```

(2) INFORMATION FOR SEQ ID NO:34:

(i) SEQUENCE CHARACTERISTICS:
       (A) LENGTH: 106 amino acids
       (B) TYPE: amino acid
       (C) STRANDEDNESS: single
       (D) TOPOLOGY: linear (ii) MOLECULE TYPE: peptide (v) FRAGMENT TYPE: internal (xi) SEQUENCE DESCRIPTION: SEQ ID NO:34:

```
Ser Ala Asn Ile Thr Ile Val Glu Ser Asn Glu Phe Ile Thr Gly Met
 1               5                  10                  15
Pro Ala Ser Thr Glu Thr Ala Tyr Val Ser Ser Glu Ser Pro Ile Arg
                20                  25                  30
Ile Ser Val Ser Thr Glu Gly Ala Asn Thr Ser Ser Ser Thr Ser Thr
            35                  40                  45
Ser Thr Thr Gly Thr Ser His Leu Ile Lys Cys Ala Glu Lys Glu Lys
        50                  55                  60
Thr Phe Cys Val Asn Gly Gly Glu Cys Phe Thr Val Lys Asp Leu Ser
 65                 70                  75                  80
```

```
            Asn  Pro  Ser  Arg  Tyr  Leu  Cys  Lys  Cys  Pro  Asn  Glu  Phe  Thr  Gly  Asp
                           85                      90                           95

Arg  Cys  Gln  Asn  Tyr  Val  Met  Ala  Ser  Phe
                           100                     105
```

( 2 ) INFORMATION FOR SEQ ID NO:35:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:35:

```
            Ala  Gly  Ser  Lys  Leu  Val  Leu  Arg  Cys  Glu  Thr  Ser  Ser  Glu  Tyr  Ser
            1                   5                      10                          15

Ser  Leu  Arg  Phe  Lys  Trp  Phe  Lys  Asn  Gly  Asn  Glu  Leu  Asn  Arg  Arg
                           20                      25                          30

Asn  Lys  Pro  Glu  Asn  Ile  Lys  Ile  Gln  Lys  Lys  Pro  Gly  Lys  Ser  Glu
                           35                      40                          45

Leu  Arg  Ile  Asn  Lys  Ala  Ser  Leu  Ala  Asp  Ser  Gly  Glu  Tyr  Met  Cys
                 50                      55                      60

Lys  Val  Ile  Ser  His  Leu  Gly  Asn  Asp  Ser  Ala  Ser  Ala  Asn  Ile  Thr
            65                      70                      75                           80

Ile  Val  Glu  Ser  Asn  Ala  Thr  Ser  Thr  Ser  Thr  Thr  Gly  Thr  Ser  His
                                85                      90                          95

Leu  Ile  Lys  Cys  Ala  Glu  Lys  Glu  Lys  Thr  Phe  Cys  Val  Asn  Gly  Gly
                           100                     105                         110

Glu  Cys  Phe  Thr  Val  Lys  Asp  Leu  Ser  Asn  Pro  Ser  Arg  Tyr  Leu  Cys
                           115                     120                         125

Lys  Cys  Pro  Asn  Glu  Phe  Thr  Gly  Asp  Arg  Cys
                           130                     135
```

( 2 ) INFORMATION FOR SEQ ID NO:36:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:36:

```
            Ala  Gly  Ser  Lys  Leu  Val  Leu  Arg  Cys  Glu  Thr  Ser  Ser  Glu  Tyr  Ser
            1                   5                      10                          15

Ser  Leu  Arg  Phe  Lys  Trp  Phe  Lys  Asn  Gly  Asn  Glu  Leu  Asn  Arg  Lys
                           20                      25                          30

Asn  Lys  Pro  Glu  Asn  Ile  Lys  Ile  Gln  Lys  Lys  Pro  Gly  Lys  Ser  Glu
                           35                      40                          45

Leu  Arg  Ile  Thr  Lys  His  Pro  Trp  Leu  Thr  Leu  Glu  Ser  Ile  Cys  Ala
                 50                      55                      60

Asn  Thr  Ser  Ser  Ser  Thr  Ser  Thr  Thr  Gly  Thr  Ser  His  Leu
            65                      70                      75                           80

Ile  Lys  Cys  Ala  Glu  Lys  Glu  Lys  Thr  Phe  Cys  Val  Asn  Gly  Gly  Glu
                           85                      90                          95
```

```
              Cys  Phe  Thr  Val  Lys  Asp  Leu  Ser  Asn  Pro  Ser  Arg  Tyr  Leu  Cys  Lys
                             100                      105                      110

Cys  Pro  Asn  Glu  Phe  Thr  Gly  Asp  Arg  Cys
                             115                      120
```

(2) INFORMATION FOR SEQ ID NO:37:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:37:

```
              Leu  Val  Lys  Cys  Ala  Glu  Lys  Glu  Lys  Thr  Phe  Cys  Val  Asn  Gly  Gly
              1                  5                      10                      15

Glu  Cys  Phe  Met  Val  Lys  Asp  Leu  Ser  Asn  Pro  Ser  Arg  Tyr  Leu  Cys
                             20                      25                      30

Lys  Cys  Pro  Asn  Glu  Phe  Thr  Gly  Asp  Arg  Cys  Gln  Asn
                             35                      40                      45
```

(2) INFORMATION FOR SEQ ID NO:38:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:38:

```
              Leu  Ile  Lys  Cys  Ala  Glu  Lys  Glu  Lys  Thr  Phe  Cys  Val  Asn  Gly  Gly
              1                  5                      10                      15

Glu  Cys  Phe  Thr  Val  Lys  Asp  Leu  Ser  Asn  Pro  Ser  Arg  Tyr  Leu  Cys
                             20                      25                      30

Lys  Cys  Pro  Asn  Glu  Phe  Thr  Gly  Asp  Arg  Cys  Gln  Asn
                             35                      40                      45
```

(2) INFORMATION FOR SEQ ID NO:39:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:39:

```
              Leu  Val  Lys  Cys  Ala  Glu  Lys  Glu  Lys  Thr  Phe  Cys  Val  Asn  Gly  Gly
              1                  5                      10                      15

Glu  Cys  Phe  Met  Val  Lys  Asp  Leu  Ser  Asn  Pro  Ser  Arg  Tyr  Leu  Cys
                             20                      25                      30

Lys  Cys  Gln  Pro  Gly  Phe  Thr  Gly  Ala  Arg  Cys  Thr  Glu
                             35                      40                      45
```

( 2 ) INFORMATION FOR SEQ ID NO:40:

( i ) SEQUENCE CHARACTERISTICS:
    ( A ) LENGTH: 45 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:40:

```
Leu Val Lys Cys Ala Glu Lys Glu Lys Thr Phe Cys Val Asn Gly Gly
1               5                   10                  15

Glu Cys Phe Thr Val Lys Asp Leu Ser Asn Pro Ser Arg Tyr Leu Cys
            20                  25                  30

Lys Cys Gln Pro Gly Phe Thr Gly Ala Arg Cys Thr Glu
        35                  40                  45
```

( 2 ) INFORMATION FOR SEQ ID NO:41:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:41:

```
Arg Asp Pro Cys Leu Arg Lys Tyr Lys Asp Phe Cys Ile His Gly Glu
1               5                   10                  15

Cys Lys Tyr Val Lys Glu Leu Arg Ala Pro Ser Cys Ile Cys His Pro
            20                  25                  30

Gly Tyr His Gly Glu Arg Cys His Gly
        35                  40
```

( 2 ) INFORMATION FOR SEQ ID NO:42:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:42:

```
Lys Asn Pro Cys Asn Ala Glu Phe Gln Asn Phe Cys Ile His Gly Glu
1               5                   10                  15

Cys Lys Tyr Ile Glu His Leu Glu Ala Val Thr Cys Lys Cys Gln Gln
            20                  25                  30

Glu Tyr Phe Gly Glu Arg Cys Gly Glu
        35                  40
```

( 2 ) INFORMATION FOR SEQ ID NO:43:

( i ) SEQUENCE CHARACTERISTICS:
    ( A ) LENGTH: 40 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:43:

```
Lys Asn Pro Cys Ala Ala Lys Gln Asn Phe Cys Ile His Gly Glu Cys
1               5                   10                  15
Arg Tyr Ile Glu Asn Leu Glu Val Val Thr Cys His Cys His Gln Asp
                20                  25                  30
Tyr Phe Gly Glu Arg Cys Gly Glu
            35              40
```

( 2 ) INFORMATION FOR SEQ ID NO:44:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:44:

```
Asp Ser Glu Cys Pro Leu Ser His Asp Gly Tyr Cys Leu His Asp Gly
1               5                   10                  15
Val Cys Met Tyr Ile Glu Ala Leu Asp Lys Tyr Ala Cys Asn Cys Val
                20                  25                  30
Val Gly Tyr Ile Gly Glu Arg Cys Gln Tyr
            35              40
```

( 2 ) INFORMATION FOR SEQ ID NO:45:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:45:

```
Phe Asn Asp Cys Pro Asp Ser His Thr Gln Phe Cys Phe His Gly Thr
1               5                   10                  15
Cys Arg Phe Leu Val Gln Glu Asp Lys Pro Ala Cys Val Cys His Ser
                20                  25                  30
Gly Tyr Val Gly Ala Arg Cys Glu His
            35              40
```

( 2 ) INFORMATION FOR SEQ ID NO:46:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:46:

```
Cys Xaa Xaa Lys Xaa Lys Xaa Phe Cys Val Asn Gly Gly Xaa Cys Xaa
1               5                   10                  15
```

```
Xaa Val Lys Asp Leu Xaa Xaa Pro Xaa Arg Tyr Leu Cys Xaa Cys Xaa
         20                  25                     30

Asn Glu Phe Thr Gly Asp Arg Cys
             35              40
```

( 2 ) INFORMATION FOR SEQ ID NO:47:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:47:

```
Cys Xaa Xaa Xaa Xaa Xaa Xaa Xaa Cys Xaa Xaa Xaa Gly Xaa Cys Xaa
1                5                   10                  15

Xaa Xaa Xaa Xaa Xaa Xaa Xaa Xaa Xaa Xaa Xaa Xaa Cys Xaa Cys Xaa
            20                  25                  30

Xaa Xaa Xaa Xaa Gly Xaa Arg Cys
         35              40
```